(12) United States Patent
Mederski et al.

(10) Patent No.: US 7,547,702 B2
(45) Date of Patent: Jun. 16, 2009

(54) 4-AMINO-QUINAZOLINES

(75) Inventors: Werner Mederski, Zwingenberg (DE); Ralf Devant, Darmstadt (DE); Maria Devant, legal representative, Darmstadt (DE); Gerhard Barnickel, Darmstadt (DE); Sabine Bernotat-Danielowski, Bad Neuheim (DE); James Vickers, Wolverhampton (GB); Bertram Cezanne, Moerfelden-Walldorf (DE); Daljit Dhanoa, Wakefield, MA (US); Bao-Ping Zhao, Plainsboro, NJ (US); James Rinker, Kenhurst, PA (US); Mark R. Player, Phoenixville, PA (US); Edward Jaegar, Trappe, PA (US); Richard Soll, Lawrenceville, NJ (US)

(73) Assignee: Ortho-McNeil Pharmaceutical, Inc., Rantan, NJ (US)

( * ) Notice: Subject to any disclaimer, the term of this patent is extended or adjusted under 35 U.S.C. 154(b) by 616 days.

(21) Appl. No.: 10/380,908

(22) PCT Filed: Sep. 17, 2001

(86) PCT No.: PCT/EP01/10705

§ 371 (c)(1),
(2), (4) Date: Jun. 30, 2005

(87) PCT Pub. No.: WO02/24667

PCT Pub. Date: Mar. 28, 2002

(65) Prior Publication Data

US 2006/0019974 A1    Jan. 26, 2006

Related U.S. Application Data

(60) Provisional application No. 60/304,188, filed on Sep. 20, 2000.

(51) Int. Cl.
*A61K 31/517*    (2006.01)
*A61K 31/535*    (2006.01)
*C07D 239/72*    (2006.01)
*C07D 413/12*    (2006.01)

(52) U.S. Cl. .......................... 514/252.14; 514/252.17; 514/266.4; 514/235.8; 544/293; 544/116

(58) Field of Classification Search .............. 514/266.4, 514/252.14, 252.17; 544/293
See application file for complete search history.

(56) References Cited

U.S. PATENT DOCUMENTS

| 3,669,968 A * | 6/1972 | Hess ..................... 544/291 |
| 4,642,347 A | 2/1987 | Kreft, III et al. |
| 4,952,567 A | 8/1990 | DeMeyts et al. |
| 5,240,940 A | 8/1993 | Arnold et al. |
| 5,245,036 A | 9/1993 | Robey et al. |
| 5,324,839 A | 6/1994 | Clemence et al. |
| 5,478,938 A | 12/1995 | Clemence et al. |
| 5,598,994 A | 2/1997 | Olewinski et al. |
| 5,817,674 A | 10/1998 | Clemence et al. |
| 5,840,695 A | 11/1998 | Frank et al. |
| 5,885,803 A | 3/1999 | Bandman et al. |
| 5,906,819 A | 5/1999 | Kaibuchi et al. |
| 5,932,470 A | 8/1999 | Frank et al. |
| 5,958,944 A | 9/1999 | Arita et al. |
| 5,972,598 A | 10/1999 | Chaudhary et al. |
| 5,977,102 A | 11/1999 | Himmelshbach et al. |
| 6,004,979 A | 12/1999 | Clemence et al. |
| 6,153,617 A | 11/2000 | Bridges |
| 6,184,226 B1 | 2/2001 | Chakravarty et al. |
| 6,207,148 B1 | 3/2001 | Bandman et al. |
| 6,218,410 B1 | 4/2001 | Uehata et al. |
| 6,277,989 B1 | 8/2001 | Chakravarty et al. |
| 6,326,373 B1 | 12/2001 | Uckun et al. |
| 6,391,874 B1 | 5/2002 | Cockerill et al. |
| 7,157,466 B2 * | 1/2007 | McClure et al. ......... 514/264.11 |
| 2001/0014679 A1 | 8/2001 | Tang et al. |
| 2001/0044442 A1 | 11/2001 | Uckun et al. |
| 2002/0055514 A1 | 5/2002 | Uckun et al. |
| 2008/0058519 A1 * | 3/2008 | Osterhout et al. ............ 544/284 |

FOREIGN PATENT DOCUMENTS

| EP | 1 034 793 | 9/2000 |
| EP | 1 163 910 | 12/2001 |
| EP | 1 174 150 | 1/2002 |
| EP | 1 177 796 | 2/2002 |
| WO | WO 95/28387 | 10/1995 |
| WO | WO 96/40142 | 12/1996 |
| WO | WO 97/03069 | 1/1997 |
| WO | WO 98/02438 | 1/1998 |
| WO | WO 99/23113 | 5/1999 |
| WO | WO 99/24440 | 5/1999 |
| WO | WO 99/35132 | 7/1999 |
| WO | WO 99/35146 | 7/1999 |
| WO | WO 99/65908 | 12/1999 |
| WO | WO 00/12497 | 3/2000 |
| WO | WO 00/13497 | 3/2000 |
| WO | WO 00/57914 | 10/2000 |
| WO | WO 0057914 | 10/2000 |
| WO | WO 01/09134 | 2/2001 |
| WO | WO 02/24667 | 3/2002 |
| WO | WO 02/30465 | 4/2002 |
| WO | WO 02/053143 | 7/2002 |

OTHER PUBLICATIONS

Vippagunta, S.R. et. al., "Crystalline solids", Advanced Drug Delivery Review, 2001, vol. 48, pp. 3-26.*

* cited by examiner

*Primary Examiner*—James O Wilson
*Assistant Examiner*—Tamthom N Truong

(57) ABSTRACT

Quinazolines of the formula (I) in which R, $R^1$, $R^2$, $R^3$, $R^4$ and Y have the meaning indicated in Patent claim 1, and their salts or solvates as glycoprotein 1bIX antagonists.

4 Claims, No Drawings

4-AMINO-QUINAZOLINES

The invention relates to substituted 4-amino-quinazolines of the formula I

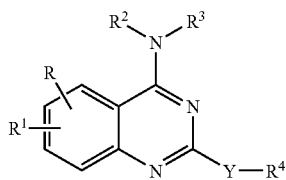

in which
R and $R^1$ are independently of each other H, A, OH, OA, Hal, $N(R^5)_2$, $NO_2$, CN, CHO, COA, $CON(R^5)_2$, $COOR^5$, allyl, $CH=CH-COOR^5$, $CH=CHCON(R^5)_2$, $SO_2A$ or phenyl, which is unsubstituted or mono-, di- or trisubstituted by A,
$R^2$ and $R^3$ are independently of each other H, A, cycloalkyl, -$Het^3$, —$(CH_2)_o$—$OR^5$, —$(CH_2)_o$—$OR^6$, —$(CH_2)_o$-Het, —$(CH_2)_o$—$NR^5$-Het, —$(CHA)_p$-$(CH_2)_o$—$N(R^5)_2$, —$(CH_2)_p$—$(CHA)_p$-$(CH_2)_m$—Ar, —$(CH_2)_o$-Z-$(CH_2)_q$—$N(R^5)_2$,

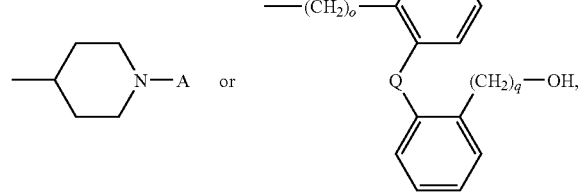

provided that $R^2$ and $R^3$ together are not H,
or $NR^2R^3$ together form a saturated monocyclic heterocyclic radical having 5 to 6 ring members, where 1 or 2 N atoms are present and the heterocyclic radical can be mono- or disubstituted by OH, Ar, OAr or arylalkyl,
$R^4$ is Ar or $Het^1$,
$R^5$ is H or A,
$R^6$ is benzo[1,3]dioxol-5-yl,
$R^7$ is H, A, cycloalkyl or —$(CH_2)_q$—$OR^5$,
Q is O or S,
Y is a direct bond, $(CH_2)_n$ or —$NR^5$—$(CH_2)_m$—,
Z is phenylene, cyclohexylene, —$NR^5$—, O, —CH(OH)—, —$CA_2$- or

A is unbranched or branched alkyl having 1 to 6 carbon atoms,
Ar is phenyl, naphthyl or biphenyl, which is unsubstituted or mono-, di- or trisubstituted by A, OH, OA, cycloalkyloxy, O—$(CH_2)_p$-Ph, $CF_3$, $OCF_3$, Hal, CN, CHO, COA, $COOR^5$, —$(CH_2)_p$—$N(R^7)_2$, $NR^5$—COA, $NO_2$, $SO_2N(R^5)_2$, mor, $SO_2$-mor, 5-methyl-3-oxo-2,4-dihydropyrazol-2-yl, naphthyl or $Het^2$,
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OH, OA, $CF_3$, $OCF_3$, $N(R^5)_2$, carbonyl oxygen, $COOR^5$, benzyl, $Het^2$ or phenyl which is unsubstituted or mono-, di- or trisubstituted by A, OH, OA, $CF_3$, $OCF_3$, Hal, CN, $COOR^5$, $N(R^5)_2$, $NO_2$, $SO_2N(R^5)_2$,
$Het^1$ is thiophen-2-yl which is substituted by Ar or $Het^2$,
$Het^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OH, OA, $CF_3$, $OCF_3$, $N(R^5)_2$, —$(CH_2)_p$—$(CHA)_p$-$N(R^5)$—$(CH_2)_q$—$COR^5$, CHO, COA or $COOR^5$,
$Het^3$ is a partially or completely unsaturated mono- or bicyclic heterocyclic radical having 5 to 10 ring members, where 1 or 2 N atoms are present and the heterocyclic radical can be mono- or disubstituted by A, Hal, OH, OA, $CF_3$, $OCF_3$, $N(R^5)_2$, $SO_2A$ or $COOR^5$ provided that the heterocyclic radical is not bonded via an N atom,
Hal is F, Cl, Br or I,
mor is morpholin-4-yl,
Ph is phenyl,
n is 1, 2, 3, 4, 5 or 6,
m is 0, 1, 2, 3, 4, 5 or 6,
o is 1, 2, 3, 4, 5, 6 or 7,
p is 0, 1, 2, 3 or 4,
q is 1, 2, 3 or 4, and their pharmaceutically tolerable salts and solvates.

Similar 4-amino substituted quinazolines are disclosed in WO 99/09986, Mastafanova, Li et al, Khim.-Farm.Zh. 1982, 16, 938-42, U.S. Pat. No. 5,436,233 or DE 2135172.

The invention is based on the object of finding novel compounds having valuable properties, in particular those which can be used for the production of medicaments.

It has been found that the compounds of the formula I and their salts or solvates have very valuable pharmacological properties together with good tolerability.

They act especially as GP1bIX inhibitors, in particular inhibiting the interaction of this receptor with the ligand von Willebrand factor (vWF). This action can be demonstrated, for example, by a method which is described by S. Meyer et al. in J. Biol. Chem. 1993, 268, 20555-20562. The property as GP1bIX alpha-thrombin receptor (N. J. Greco, Biochemistry 1996, 35, 915-921) can also be blocked by the compounds mentioned.

The significance of GP1bIX as an adhesion receptor on platelets, which mediates the primary interaction of platelets with an arteriosclerotically modified vascular wall via binding to the vWF expressed there, has been described by many authors (e.g. Z. M. Ruggeri in Thromb. Hemost. 1997, 78, 611-616). The activation of another platelet adhesion receptor, GPIIbIIIa, following the GP1bIX-vWF interaction, leads to platelet aggregation and thus to thrombotic vascular occlusion.

A GP1bIX antagonist can thus prevent the start of thrombus formation and thus also release of active substances from the platelets which, for example, promote thrombus growth and have an additional trophic action on the vascular wall. This has been shown with inhibitory peptides or antibodies in various experimental models (e.g. H Yamamoto et al., Thromb. Hemost. 1998, 79, 202-210).

In the case of higher shear forces, the blocking action of GP1bIX inhibitors exerts its maximum effect, as described by J. J. Sixma et al. in Arteriosclerosis, Thrombosis, and Vascular Biology 1996, 16, 64-71. According to the flow chamber method used there, the compounds of the formula I can be characterized as GP1bIX inhibitors in whole blood.

The inhibition of thrombus formation of the GP1bIX inhibitors can be measured by a modified Born method (Nature 1962, 4832, 927-929) using botrocetin or ristocetin as an aggregation stimulant.

The compounds of the formula I according to the invention can therefore be employed as pharmaceutical active compounds in human and veterinary medicine. They act as adhesion receptor antagonists, in particular as glycoprotein 1bIX antagonists, and are suitable for the prophylaxis and/or therapy of thrombotic disorders and sequelae deriving therefrom. The preferentially best action is to be expected in the case of thrombotic disorders in the arterial vascular system, but GP1bIX inhibitors also have an effect in the case of thrombotic disorders in the venous vascular bed. The disorders are acute coronary syndromes, angina pectoris, myocardial infarct, peripheral circulatory disorders, stroke, transient ischaemic attacks, arteriosclerosis, reocclusion/restenosis after angioplasty/stent implantation. The compounds can furthermore be employed as anti-adhesive substances where the body comes into contact with foreign surfaces such as implants, catheters or cardiac pacemakers.

Therefore, the invention relates further to compounds of the formula I according to claim 1 and their physiologically acceptable salts or solvates as pharmaceutical active compounds.

The invention relates to compounds of the formula I according to claim 1 and their physiologically acceptable salts or solvates as glycoprotein 1bIX antagonists.

Comparison medication introduced onto the market which may be mentioned are aspirin and GPIIbIIIa antagonists.

The invention relates to the compounds of the formula I and their salts or solvates, and to a process for the preparation of these compounds and their salts or solvates, characterized in that
a) a compound of the formula I is liberated from one of its functional derivatives by treating with a solvolysing or hydrogenolysing agent, or
b) for compounds in which Y is a direct bond or $(CH_2)_n$ in stage 1) a compound of the formula II

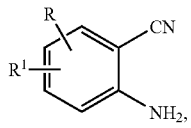

in which
R and $R^1$ have a meaning indicated in claim 1, is reacted with a compound of the formula III

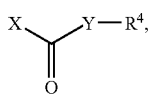

in which $R^4$ has a meaning indicated in claim 1 and Y is a direct bond or $(CH_2)_n$,
and X is Cl, Br, —OH or a reactive esterified OH group followed by converting the cyano group to an amide group by conventional means to give a compound of formula IV

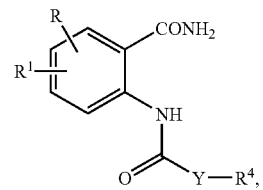

in which R, $R^1$ and $R^4$ have a meaning indicated in claim 1 and Y is a direct bond or $(CH_2)_n$,
in stage 2) a compound of formula IV as indicated above is reacted with a base to give a compound of formula V

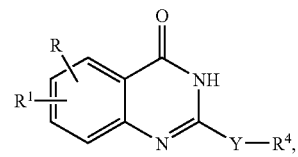

in which R, $R^1$ and $R^4$ have a meaning indicated in claim 1 and Y is a direct bond or $(CH_2)_n$,
in stage 3) a compound of formula V as indicated above is reacted with a chlorinating agent to give a compound of formula VI

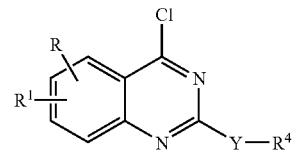

in which R, $R^1$ and $R^4$ have a meaning indicated in claim 1 and Y is a direct bond or $(CH_2)_n$,
and in stage 4) a compound of formula VI as indicated above is reacted with a compound of formula VII

in which $R^2$ and $R^3$ or $NR^2R^3$ have a meaning indicated in claim 1, or
b) for compounds in which Y is $NR^5$—$(CH_2)_m$—, in stage 1) a compound of the formula VIII

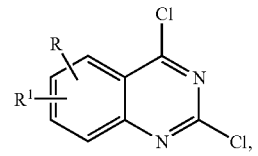

in which
R and $R^1$ have a meaning indicated in claim 1, is reacted with a compound of formula VII

VII in which $R^2$ and $R^3$ or $NR^2R^3$ have a meaning indicated in claim 1, to give a compound of formula IX

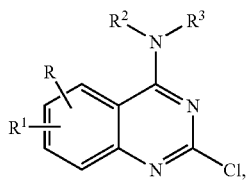
IX in which R, $R^1$, $R^2$, $R^3$ and $NR^2R^3$ have a meaning indicated in claim 1, and in stage 2) a compound of formula IX as indicated above is reacted with a compound of formula X

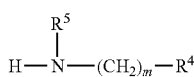
X in which $R^4$, $R^5$ and m have a meaning indicated in claim 1
or
d) a radical R, $R^1$, $R^2$, $R^3$ and or $R^4$ is converted into another radical R, $R^1$, $R^2$, $R^3$ and/or $R^4$ by, for example
reducing a nitro group, sulfonyl group or sulfoxyl group,
etherifying an OH group or subjecting an OA group to ether cleavage,
alkylating a primary or secondary amino group,
partially or completely hydrolysing a CN group,
cleaving an ester group or esterifying a carboxylic acid radical,
reacting an aryl bromide, aryl iodide, heteroaryl bromide or heteroaryliodide to give the corresponding coupling products by means of a Suzuki coupling with boronic acids,
reacting a iodoquinazoline or bromoquinazoline to give the corresponding coupling products by means of a Stille coupling with allyltributyltin,
reacting a iodoquinazoline or bromoquinazoline to give the corresponding coupling products by means of a Heck coupling with acrylates,
or carrying out a nucleophilic or electrophilic substitution, or a base or acid of the formula I is converted into one of its salts or solvates.

The compounds of the formula I can have a chiral center and therefore occur in a number of stereoisomeric forms. All these forms (e.g. R and S forms) and their mixtures (e.g. the RS forms) are included in the formula I.

The compounds according to the invention also include so-called prodrug derivatives, i.e. compounds of the formula I modified with, for example, alkyl or acyl groups, sugars or oligopeptides and which are rapidly cleaved in the body to give the active compounds according to the invention.

Furthermore, free amino groups as substituents of compounds of the formula I can be provided with appropriate conventional protective groups.

Solvates of the compounds of the formula I are understood as meaning adducts of inert solvent molecules to the compounds of the formula I which are formed on account of their mutual power of attraction. Solvates are, for example, mono- or dihydrates or alcoholates.

The abbreviations used have the following meanings:

| | |
|---|---|
| Ac | acetyl, |
| Bu | n-butyl, |
| DBU | 1,8-diazabicyclo[5.4.0]undec-7-ene, |
| DMA | dimethylacetamide, |
| DMF | dimethylformamide, |
| dppf | 1,1'-bis(diphenylphosphino)ferrocene, |
| Et | ethyl, |
| iPr | isopropyl, |
| Me | methyl, |
| Ph | phenyl, |
| TEA | triethylamine, |
| TFA | trifluoroacetic acid. |

In the above formulae, A is alkyl and has 1 to 6, preferably 1, 2, 3 or 4 C atoms. Alkyl is preferably methyl, furthermore ethyl, propyl, isopropyl, butyl, isobutyl, sec-butyl or tert-butyl, additionally also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

A is preferentially methyl, ethyl, propyl, isopropyl, butyl or pentyl.

Ar is phenyl, naphthyl or biphenyl, which is unsubstituted or mono-, di- or trisubstituted by A, OH, OA, cycloalkyloxy, O—$(CH_2)_p$-Ph, $CF_3$, $OCF_3$, Hal, CN, CHO, COA, $COOR^5$, —$(CH_2)_p$—$N(R^7)_2$, $NR^5$—COA, $NO_2$, $SO_2N(R^5)_2$, mor, $SO_2$-mor, 5-methyl-3-oxo-2,4-dihydropyrazol-2-yl, naphthyl or $Het^2$.

Ar is preferentially phenyl, preferably—as indicated—mono- di- or trisubstituted phenyl, specifically preferentially phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2-, 3- or 4-tert-butylphenyl, 2-, 3- or 4-aminophenyl, 2-, 3- or 4-N,N-dimethylaminophenyl, 2-, 3- or 4-sulfamoylphenyl, 2-, 3- or 4-nitrophenyl, 2-, 3- or 4-hydroxyphenyl, 2-, 3- or 4-methoxyphenyl, 2-, 3- or 4-ethoxyphenyl, 2-, 3- or 4-pentoxyphenyl, 2-, 3- or 4-phenoxyphenyl, 2-, 3- or 4-phenylmethoxyphenyl, 2-, 3- or 4-trifluoromethylphenyl, 2-, 3- or 4-trifluoromethoxyphenyl, 2-, 3- or 4-cyclopentyloxyphenyl, 2-, 3- or 4-carboxyphenyl, 2-, 3- or 4-(N,N-diethyl)sulfamoylphenyl, 4-(3-methyl-butyramido)-phenyl, 2-, 3- or 4-cyanophenyl, 2-, 3- or 4-fluorophenyl, 2-, 3- or 4-chlorophenyl, 2-, 3- or 4-bromophenyl, 2,3-, 2,4-, 2,5-, 2,6-, 3,4- or 3,5-dichlorophenyl, 2,3-, 2,4-, 2,5-, 2,6-, 3,4- or3,5-dibromophenyl, 2,3-, 2,4-, 2,5-, 2,6-, 3,4- or 3,5-dimethoxyphenyl, 2,3-, 2,4-, 2,5-, 2,6-, 3,4- or 3,5-di(trifluoromethyl)phenyl, 2,3-, 2,4-, 2,5-, 2,6-, 3,4- or 3,5-di(phenylmethoxy)phenyl, 2-chloro-6-methylphenyl, 2-chloro-4-fluorophenyl, 3-bromo-6-fluorophenyl, 3,4,5-trimethoxyphenyl, 4-(morpholin-4-yl)phenyl, 4-(morpholin-4-yl-sulfonyl)phenyl, 4-(5-methyl-3-oxo-2,4-dihydropyrazol-2-yl)phenyl, 4-(4,6-dimethoxy-pyrimidin-2-yl)phenyl, 3-(4,6-dimethoxy-pyrimidin-2-yl)phenyl, 4-(pyrid-3-yl)phenyl, 3-(pyrid-3-yl)phenyl, 4-(thiophen-2-yl)phenyl, 4-(thiophen- 3-yl)phenyl, 4-(2-formyl-thiophen-3-yl)phenyl, 3-(thiophen-2-yl)phenyl, 4-(benzo[c]thiophen-2-yl)phenyl, 4-(naphthalen-1-yl)phenyl or

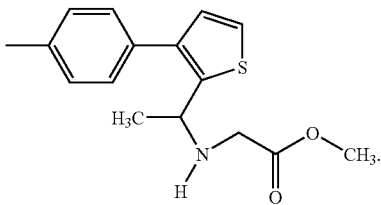

Furthermore, however, Ar is also preferentially unsubstituted naphthyl or biphenyl—as indicated—or alternatively mono-, di- or trisubstituted biphenyl, specifically preferentially biphenyl-4-yl or biphenyl-3-yl, 2'-methylbiphenyl-4-yl, 3'-methylbiphenyl-4-yl, 4'-methylbiphenyl-4-yl, 2'-methylbiphenyl-3-yl, 3'-methylbiphenyl-3-yl, 4'-methylbiphenyl-3-yl, 2-methylbiphenyl-4-yl, 3-methylbiphenyl-4-yl, 2-methylbiphenyl-3-yl, 4-methylbiphenyl-3-yl, 2'-tert-butylbiphenyl-4-yl, 3'-tert-butylbiphenyl-4-yl, 4'-tert-butylbiphenyl-4-yl, 2'-tert-butylbiphenyl-3-yl, 3'-tert-butylbiphenyl-3-yl, 4'-tert-butylbiphenyl-3-yl, 2-tert-butylbiphenyl-4-yl, 3-tert-butylbiphenyl-4-yl, 2-tertbutylbiphenyl-3-yl, 4-tert-butylbiphenyl-3-yl, 2'-isopropylbiphenyl-4-yl, 3'-isopropylbiphenyl-4-yl, 4'-isopropylbiphenyl-4-yl, 2'-isopropylbiphenyl-3-yl, 3'-isopropylbiphenyl-3-yl, 4'-isopropylbiphenyl-3-yl, 2-isopropylbiphenyl-4-yl, 3-isopropylbiphenyl-4-yl, 2-isopropylbiphenyl), 4-isopropylbiphenyl-3-yl, 2'-fluorobiphenyl-4-yl, 3'-fluorobiphenyl-4-yl, 4'-fluorobiphenyl-4-yl, 2'-fluorobiphenyl-3-yl, 3'-fluorobiphenyl-3-yl, 4'-fluorobiphenyl-3-yl, 2-fluorobiphenyl-4-yl, 3-fluorobiphenyl-4-yl, 2-fluorobiphenyl-3-yl, 4-fluorobiphenyl-3-yl, 2'-chlorobiphenyl-4-yl, 3'-chlorobiphenyl-4-yl, 4'-chlorobiphenyl-4-yl, 2'-chlorobiphenyl-3-yl, 3'-chlorobiphenyl-3-yl, 4'-chlorobiphenyl-3-yl, 2-chlorobiphenyl-4-yl, 3-chlorobiphenyl-4-yl, 2-chlorobiphenyl-3-yl, 4-chlorobiphenyl-3-yl, 2'-methoxybiphenyl-4-yl, 3'-methoxybiphenyl-4-yl, 4'-methoxybiphenyl-4-yl, 2'-methoxybiphenyl-3-yl, 3'-methoxybiphenyl-3-yl, 4'-methoxybiphenyl-3-yl, 2-methoxybiphenyl-4-yl, 3-methoxybiphenyl-4-yl, 2-methoxybiphenyl-3-yl, 4-methoxybiphenyl-3-yl, 2'-nitrobiphenyl-4-yl, 3'-nitrobiphenyl-4-yl, 4'-nitrobiphenyl-4-yl, 2'-nitrobiphenyl-3-yl, 3'-nitrobiphenyl-3-yl, 4'-nitrobiphenyl-3-yl, 2-nitrobiphenyl-4-yl, 3-nitrobiphenyl-4-yl, 2-nitrobiphenyl-3-yl, 4-nitrobiphenyl-3-yl, 2'-trifluoromethylbiphenyl-3-yl, 3'-trifluoromethylbiphenyl-4-yl, 4'-trifluoromethyl-biphenyl-4-yl, 2'-trifluoromethylbiphenyl-3-yl, 3'-trifluoromethylbiphenyl-3-yl, 4'-trifluoromethylbiphenyl-3-yl, 2-trifluoromethylbiphenyl-4-yl, 3-trifluoromethylbiphenyl-4-yl, 2-trifluoromethylbiphenyl-3-yl, 4-trifluoromethylbiphenyl-3-yl, 2'-trifluoromethoxybiphenyl-4-yl, 3'-trifluoromethoxybiphenyl-4-yl, 4'-trifluoromethoxybiphenyl-4-yl, 2'-trifluoromethoxybiphenyl-3-yl, 3'-trifluoromethoxybiphenyl-3-yl, 4'-trifluoromethoxybiphenyl-3-yl, 2-trifluoromethoxybiphenyl-4-yl, 3-trifluoromethoxybiphenyl-4-yl, 2-trifluoromethoxybiphenyl-3-yl, 4-trifluoromethoxybiphenyl-3-yl, 3'-acetylbiphenyl-4-yl, 3'-acetylaminobiphenyl-4-yl, 3'-aminobiphenyl-4-yl, 3'-formylbiphenyl-4-yl, 4'-formylbiphenyl-4-yl, 4'-propylaminomethylbiphenyl-4-yl, 3'-methoxyethylaminomethylbiphenyl-4-yl, 4'-cyclohexylmethylaminomethylbiphenyl-4-yl or 3'-hydroxypropylaminomethylbiphenyl-4-yl, furthermore preferentially disubstituted biphenyls, such as 2'-methyl-3'-nitrobiphenyl-4-yl, 2'-methyl-4'-nitrobiphenyl-4-yl, 2'--methyl-5'-nitrobiphenyl-4-yl, 2'-methyl-6'-nitrobiphenyl-4-yl, 3'-methyl-2'-nitrobiphenyl-4-yl, 3'-methyl-4'-nitrobiphenyl-4-yl, 3'-methyl-5'-nitrobiphenyl-4-yl, 3'-methyl-6'- nitrobiphenyl-4-yl, 4'-methyl-2'-nitrobiphenyl-4-yl, 4'-methyl-3'-nitrobiphenyl-4-yl, 2'-methyl-3'-nitrobiphenyl-3-yl, 2'-methyl-4'-nitrobiphenyl-3-yl, 2'-methyl-5'-nitrobiphenyl-3-yl, 2'-methyl-6'-nitrobiphenyl-3-yl, 3'-methyl-2'-nitrobiphenyl-3-yl, 3'-methyl-4'-nitrobiphenyl-3-yl, 3'-methyl-5'-nitrobiphenyl-3-yl, 3'-methyl-6'-nitrobiphenyl-3-yl, 4'-methyl-2'-nitrobiphenyl-3-yl, 4'-methyl-3'-nitrobiphenyl-3-yl, 2'-methoxy-2-methylbiphenyl-4-yl, 3'-methoxy-2-methylbiphenyl-4-yl, 4'-methoxy-2-methylbiphenyl-4-yl, 4'-methoxy-3-nitrobiphenyl-4-yl, 2'-chloro-3'-fluorobiphenyl-4-yl, 2'-chloro-4'- fluorobiphenyl-4-yl, 2'-chloro-5'-fluorobiphenyl-4-yl, 2'-chloro-6'-fluorobiphenyl-4-yl, 3'-chloro-2'-fluorobiphenyl-4-yl, 3'-chloro-4'-fluorobiphenyl-4-yl, 3'-chloro-5'-fluorobiphenyl-4-yl, 3'-chloro-6'-fluorobiphenyl-4-yl, 4'-chloro-2'-fluorobiphenyl-4-yl, 4'-chloro-3'-fluorobiphenyl-4-yl, 2'-chloro-3'-fluorobiphenyl-3-yl, 2'-chloro-4'-fluorobiphenyl-3-yl, 2'-chloro-5'-fluorobiphenyl-3-yl, 2'-chloro-6'-fluorobiphenyl-3-yl, 3'-chloro-2'-fluorobiphenyl-3-yl, 3'-chloro-4'-fluorobiphenyl-3-yl, 3'-chloro-5'-fluorobiphenyl-3-yl, 3'-chloro-6'-fluorobiphenyl-3-yl, 4'-chloro-2'-fluorobiphenyl-3-yl, 4'-chloro-3'- fluorobiphenyl-3-yl, (2,3'-diethyl)biphenyl-4-yl, (3,3'-diethyl)biphenyl-4-yl), (2,2'-diethyl)biphenyl-4-yl, (2,4'-diethyl)biphenyl-4-yl, (2',3'-dimethoxy)biphenyl-4-yl, (2',4'-dimethoxy)biphenyl-4-yl, (2',5'-dimethoxy)biphenyl-4-yl, (2',6'-dimethoxy)-biphenyl-4-yl, (3',4'-dimethoxy)biphenyl-4-yl, (3',5'-dimethoxy)biphenyl-4-yl, (2',3'-dimethoxy)-biphenyl-3-yl, (2',4'-dimethoxy)biphenyl-3-yl, (2',5'-dimethoxy)biphenyl-3-yl, (2',6'-dimethoxy)-biphenyl-3-yl, (3',4'-dimethoxy)biphenyl)-3-yl, (3',5'-dimethoxy)biphenyl-3-yl, (3',5'-dichloro)biphenyl-4-yl, (3',5'-dichloro)biphenyl-3-yl, (2',4'-dichloro)biphenyl-4-yl, (3',4',5'-trimethoxy)biphenyl-4-yl, (2',3'-di(trifluoromethyl))biphenyl-4-yl, (2',4'-di(trifluoromethyl))biphenyl-4-yl, (2',5'-di(trifluoromethyl)) biphenyl-4-yl, (2',6'-di(trifluoromethyl))biphenyl-4-yl, (3',4'-di(trifluoromethyl))biphenyl-4-yl, (3',5'-di (trifluoromethyl))biphenyl-4-yl, (2',3'-di(trifluoromethyl)) biphenyl-3-yl, (2',4'-di(trifluoromethyl))biphenyl-3-yl, (2',5'-di(trifluoromethyl))biphenyl-3-yl, (2',6'-di (trifluoromethyl))biphenyl-3-yl, (3',4'-di(trifluoromethyl)) biphenyl-3-yl, (3',5'-di(trifluoromethyl)biphenyl-3-yl, (2,2'-dimethyl)biphenyl-4-yl, (2,'3-dimethyl)biphenyl-4-yl, (2,4'-dimethyl)biphenyl-4-yl, (2,2'-dimethyl)biphenyl-3-yl, (2,3'-dimethyl)biphenyl-3-yl or (2,4'-dimethyl)biphenyl-3-yl.

Phenyl, 2'-, 3- or 4-fluorophenyl, 2-, 3- or 4-chlorophenyl, 4-bromophenyl, 2,4- or 3,4-dichlorophenyl, 2,5- or 3,4-dimethoxyphenyl, 3,5-bis(trifluoromethyl)phenyl, 4-aminophenyl, 4-dimethylaminophenyl, 2-, 3- or 4-methylphenyl, 2-, 3- or 4-methoxyphenyl, 4-propylphenyl, 4-isopropylphenyl, 4-butylphenyl, 4-tert.-butylphenyl, 2-, 3- or 4-nitrophenyl, 2-cyanophenyl, 2-, 3- or 4-pentoxyphenyl, 3- or 4-phenoxyphenyl, 2- or 4-benzyloxyphenyl, 2-, 3- or 4-trifluoromethylphenyl, 2-, 3- or 4-trifluoromethoxyphenyl, 2- or 4-cyclopentyloxyphenyl, 3- or 4-carboxyphenyl, 2-, 3- or 4-(N,N-diethyl)sulfamoylphenyl, 3,4-di(benzyloxy)phenyl, 4-(3-methyl-butyramido)-phenyl, 2-chloro-6-methylphenyl, 2-chloro-4-fluorophenyl, 3-bromo-6-fluorophenyl, 3,4,5-trimethoxyphenyl, 4-(morpholin-4-yl)phenyl, 4-(morpholin-4-yl-sulfonyl)phenyl, 4-(5-methyl-3-oxo-2,4-dihydropyrazol-2-yl)phenyl, 4-(4,6-dimethoxy-pyrimidin-2-yl)phenyl, 3-(4,6-dimethoxy-pyrimidin-2-yl)phenyl, 4-(pyridin-3-yl)phenyl, 3-(pyridin-3-yl)phenyl, 4-(thiophen-2-yl)phenyl, 3-(thiophen-2-yl)phenyl, 4-(benzo[c]thiophen-2-yl)phenyl, 4-(naphthalen-1-yl)phenyl, 4-(thiophen-3-yl) phenyl, 4-(2-formyl-thiophen-3-yl)phenyl, naphthyl, biphenyl-4-yl, 2'-fluorobiphenyl-4-yl, 4'-fluorobiphenyl-4-yl, 4'-fluorobiphenyl-3-yl, 4'-chlorobiphenyl-4-yl, 4'-chlorobiphenyl-3-yl, 4'-methoxybiphenyl-4-yl, 4'-methoxybiphenyl-3-yl, 3'-nitrobiphenyl-4-yl, 3'-acetylbiphenyl-4-yl, 3'-acetylaminobiphenyl-4-yl, 3'-aminobiphenyl-4-yl, 3'-formylbiphenyl-4-yl, 4'-formylbiphenyl-4-yl, 4'-propylaminomethylbiphenyl-4-yl, 3'-methoxyethyl-aminomethylbiphenyl-4-yl, 4'-cyclohexylmethylaminomethylbiphenyl-4-yl, 3'-hydroxypropylaminomethylbiphenyl-4-yl, (2,3'-diethyl)biphenyl-4-yl, (2,4'-diethyl)biphenyl-4-yl, (2,2'-diethyl)biphenyl-4-yl, (3',5'-dichloro)biphenyl-3-yl, (3',4'-dimethoxy)biphenyl-4-yl, (2',4'-dichloro)biphenyl-4-yl, (3',4',5'-trimethoxy)biphenyl-4-yl, (3',5'-di(trifluoromethyl))biphenyl-4-yl or

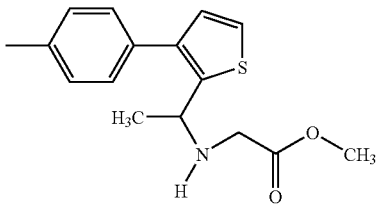

is particularly preferred for Ar.

Arylalkyl is preferentially benzyl. O—$(CH_2)_p$-Ph is phenylalkyloxy, in which p can be 0, 1, 2, 3 or 4. Benzyloxy or phenyloxy is particularly preferred.

Cycloalkyl preferably has 3-7 C atoms and is preferably cyclopropyl, cyclobutyl, cyclopentyl or cyclohexyl, and further also cyclopentylmethyl, cyclopentylethyl or cyclohexylmethyl; cyclopentyl, cyclohexylmethyl or cyclohexyl are particularly preferred.

Hal is preferably F, Cl, Br or I.

Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OH, OA, $CF_3$, $OCF_3$, $N(R^5)_2$, carbonyl oxygen, $COOR^5$, $Het^2$, benzyl or phenyl which is unsubstituted or mono-, di- or trisubstituted by A, OH, OA, $CF_3$, $OCF_3$, Hal, CN, $COOR^5$, $N(R^5)_2$, $NO_2$, $SO_2N(R^5)_2$.

Het is preferably unsubstituted 2- or 3-furyl, 2- or 3-thiophenyl, 1-,2-or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothiophenyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or completely hydrogenated. Het can thus also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thiophenyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, -4-, -5-, -6-, -7-1H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl which can be substituted as indicated above or particularly substituted by A, OA, carbonyl oxygen, $NO_2$, $Het^2$ or phenyl which is substituted by Hal, CN or OA.

Thiophen-2-yl, tetrahydro-furan-2-yl, 1-methyl-octahydro-indol-3-yl, benzo[1,3]dioxol-5-yl, piperazin-1-yl, 4-methyl-piperazin-1-yl, piperidin-1-yl, piperidin-4-yl, 1-methyl-piperidin-3-yl, 4-benzyl-piperidin-1-yl, 2-methyl-piperidin-1-yl, 1-ethyl-pyrrolidin-2-yl, 1-methyl-pyrrolidin-2-yl, 2-oxo-pyrrolidin-1-yl, pyridin-2-yl, pyridin-4-yl, 5-nitro-pyridin-2-yl, imidazol-1-yl, morpholin-4-yl, 5-methoxy-1H-indol-2-yl is particularly preferred for Het.

$Het^1$ is thiophen-2-yl which is substituted by Ar or $Het^2$, in which Ar and $Het^2$ have one of the above or below mentioned meanings. 5-(4-Fluorophenyl)-thiophen-2-yl, 5-(2-methoxyphenyl)-thiophen-2-yl, 5-(2-cyanophenyl)-thiophen-2-yl, 5-(2,5-dimethoxyphenyl)-thiophen-2-yl, 2-[2,2']bithiophenyl-5-yl, 5-(pyridin-4-yl)-thiophen-2-yl, 5-(1H-indol-5-yl)-thiophen-2-yl, 5-quinolin-8-yl-thiophen-2-yl or 5-(benzo[b]thiophen-2-yl)-thiophen-2-yl is particularly preferred for $Het^1$.

$Het^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by A, Hal, OH, OA, $CF_3$, $OCF_3$, $N(R^5)_2$, —$(CH_2)_p$—$(CHA)_p$-$N(R^5)$—$(CH_2)_q$—$COR^5$, CHO, COA or $COOR^5$.

Thiophen-2-yl, 2-formyl-thiophen-3-yl, pyridin-3-yl, pyridin-2-yl, pyridin-4-yl, indol-5-yl, quinolin-8-yl, 4,6-dimethoxy-pyrimidin-2-yl, benzo[b]thiophen-2-yl or

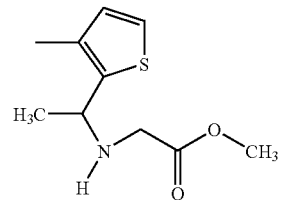

is particularly preferred for $Het^2$.

$Het^3$ is a partially or completely unsaturated mono- or bicyclic heterocyclic radical having 5 to 10 ring members, where 1 or 2 N atoms are present and the heterocyclic radical can be mono- or disubstituted by A, Hal, OH, OA, $CF_3$, $OCF_3$, $N(R^5)_2$, $SO_2A$ or $COOR^5$ provided that the heterocyclic radical is not bondend via an N atom.

Quinolin-5-yl and 1-methanesulfonyl-2,3-dihydro-1H-indol-5-yl is particularly preferred for $Het^3$.

$(CH_2)_o$-Het is preferentially thiophen-2-yl-ethyl, tetrahydro-furan-2-yl-methyl, 1-methyl-octahydro-indol-3-yl-methyl, 1-methyl-octahydro-indol-3-yl-ethyl benzo[1,3]dioxol- 5-yl-methyl, benzo[1,3]dioxol-5-yl-ethyl, piperazin-1-yl-ethyl, 4-methyl-piperazin-1-yl-propyl, piperidin-1-yl-ethyl, piperidin-4-yl-methyl, 1-methyl-piperidin-3-yl-ethyl, 4-benzyl-piperidin-1-yl-ethyl, 2-methyl-piperidin-1-yl-propyl, 1-ethyl-pyrrolidin-2-yl-methyl, 1-methyl-pyrrolidin-2-yl-methyl, 2-oxo-pyrrolidin-1-yl-propyl, pyridin-2-yl-ethyl, pyridin-4-yl-methyl, pyridin-4-yl-ethyl, imidazol-1-yl-propyl, morpholin-4-yl-propyl or morpholin-4-yl-ethyl.

$(CH_2)_o$—$NR^5$-Het is preferentially (5-nitro-pyridin-2-yl)-amino-ethyl.

$(CH_2)_o$—$OR^5$ is preferentially $(CH_2)_2$—$OCH_3$, $(CH_2)_3$—$OCH_3$ or $(CH_2)_3$—$O(iPr)$.

$(CH_2)_o$—$OR^6$ is preferentially

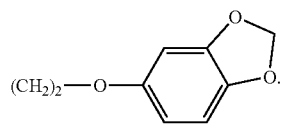

$(CH_2)_o$-Z-$(CH_2)_q$—$N(R^5)_2$ is preferentially

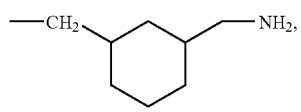

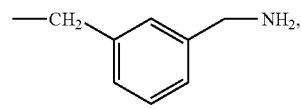

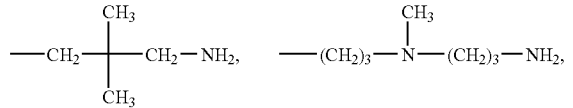

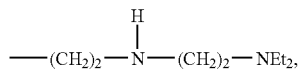

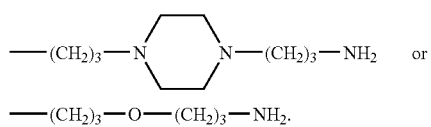

$(CH_2)_p$—$(CHA)_p$-$(CH_2)_m$—Ar is preferentially phenyl,

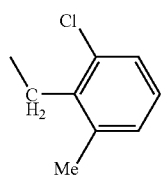

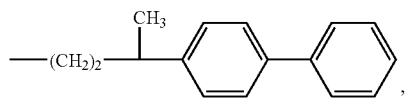

-continued

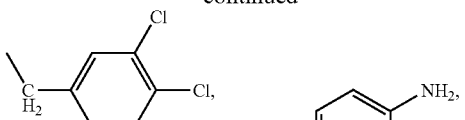

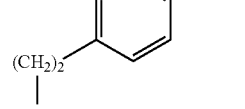

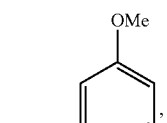

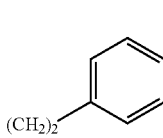

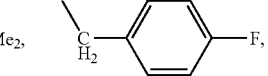

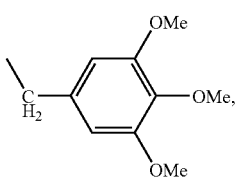

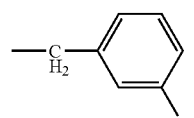

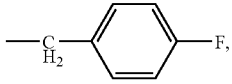

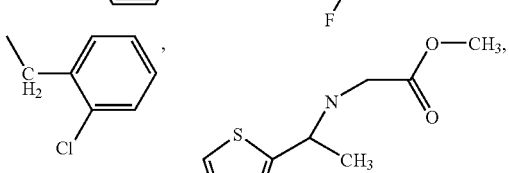

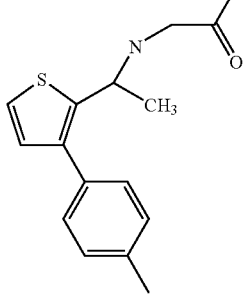

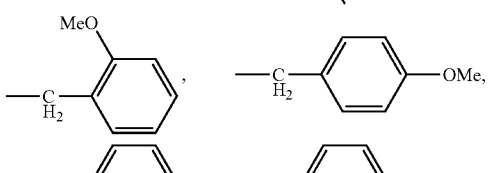

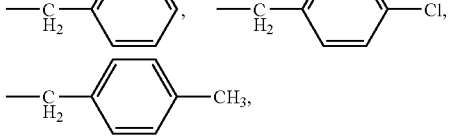

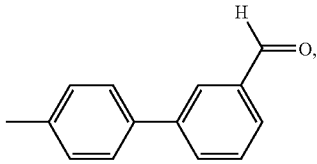

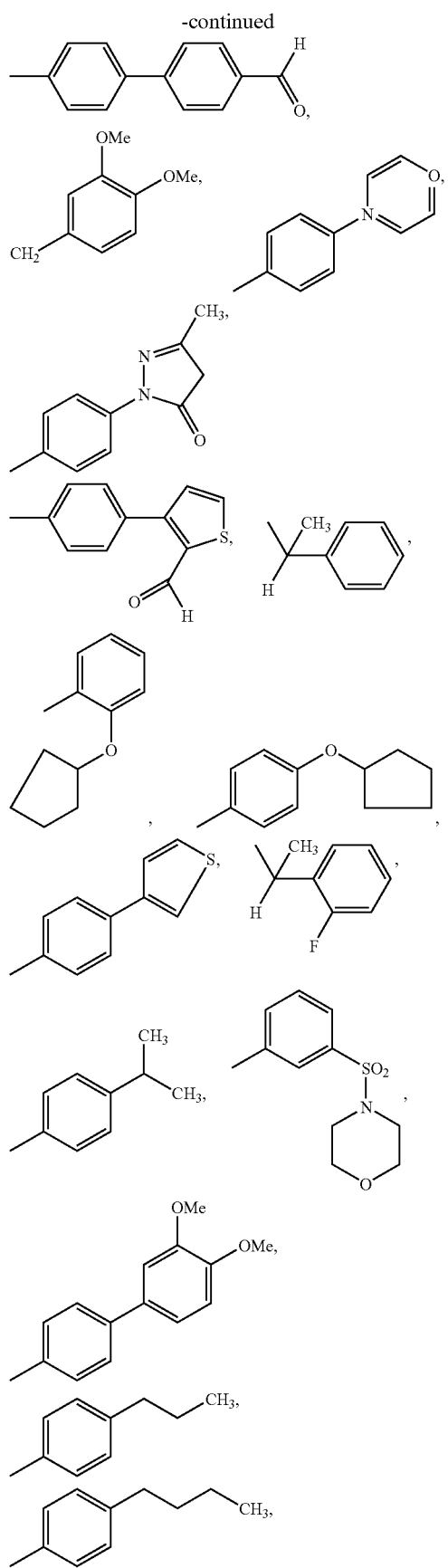

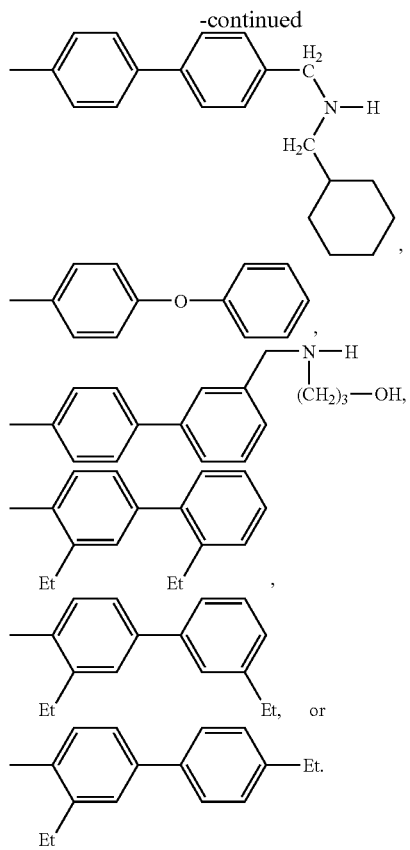

R and R¹ are independently of each other H, A, OH, OA, Hal, $N(R^5)_2$, $NO_2$, CN, CHO, COA, $CON(R^5)_2$, $COOR^5$, allyl, CH=CH—$COOR^5$, CH=CHCON$(R^5)_2$, $SO_2A$ or phenyl, which is unsubstituted or mono-, di- or trisubstituted by A, where A and Hal have a preferred meaning indicated beforehand and $R^5$ have a preferred meaning indicated in the following.

R is preferentially H or OA.

R¹ is preferentially H, A, OA, Hal, allyl, CH=CH—$COOR^5$, CH=CHCON$(R^5)_2$ or phenyl, which is unsubstituted or monosubstituted by A. H, A, OA or Cl is particularly preferred for R¹.

The preferred position of R¹ is the 6- or 7-position of the quinazoline ring system.

$R^2$ and $R^3$ are independently of each other H, A, cycloalkyl, -Het³, —$(CH_2)_o$—$OR^5$, —$(CH_2)_o$—$OR^6$, —$(CH_2)_o$-Het, —$(CH_2)_o$—$NR^5$-Het, —$(CHA)_p$-$(CH_2)_o$—$N(R^5)_2$, —$(CH_2)_p$—$(CHA)_p$-$(CH_2)_m$—Ar, —$(CH_2)_o$-Z-$(CH_2)_q$—$N(R^5)_2$,

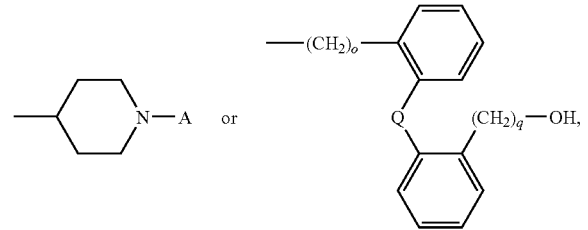

provided that $R^2$ and $R^3$ together are not H, where A, Ar, cycloalkyl, Het or Het³ have a preferred meaning indicated beforehand and $R^5$, $R^6$, Q, Z, m, o, p and q have a preferred meaning indicated in the following.

$R^2$ is preferentially H or A.

$R^3$ is preferentially A, cycloalkyl, -Het³, —$(CH_2)_o$—$OR^5$, —$(CH_2)_o$—$OR^6$, —$(CH_2)_o$-Het, —$(CH_2)_o$—$NR^5$-Het, —$(CHA)_p$-$(CH_2)_o$—$N(R^5)_2$, —$(CH_2)_p$—$(CHA)_p$-$(CH_2)_m$—Ar, —$(CH_2)_o$-Z-$(CH_2)_q$—$N(R^5)_2$,

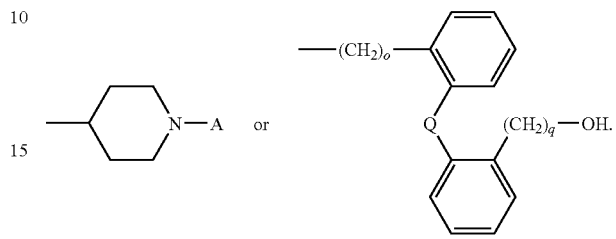

Furthermore $NR^2R^3$ together form a saturated monocyclic heterocyclic radical having 5 to 6 ring members, where 1 or 2 N atoms are present and the heterocyclic radical can be mono- or disubstituted by OH, Ar, OAr or arylalkyl, where Ar or arylalkyl have a preferred meaning indicated beforehand.

Preferred saturated monocyclic heterocyclic radicals can be piperidine or piperazine.

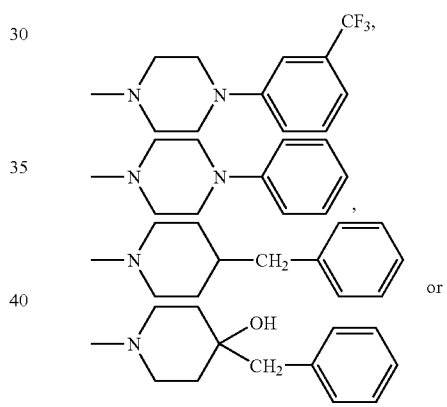

are particularly preferred for $NR^2R^3$.

$R^4$ is Ar or Het¹, where Ar or Het¹ have a preferred meaning indicated beforehand. Phenyl, 4-bromophenyl, 3,5-bis-(trifluoromethyl)phenyl, 4-tert.-butylphenyl, 3-bromo-6-fluorophenyl, 4-(pyridin-3-yl)phenyl, 3-(pyridin-3-yl)phenyl, 4-(thiophen-2-yl)phenyl, 3-(thiophen-2-yl)phenyl, naphthyl, biphenyl-4-yl, 4'-fluorobiphenyl-4-yl, 4'-fluorobiphenyl-3-yl, 4'-chlorobiphenyl-4-yl, 4'-chlorobiphenyl-3-yl, 4'-methoxybiphenyl-4-yl, 4'-methoxybiphenyl-3-yl, (3',5'-dichloro)biphenyl-3-yl is particularly preferred as Ar in $R^4$.

Phenyl, 4-bromophenyl, 3,5-bis-(trifluoromethyl)phenyl, 4-tert.-butylphenyl, 3-bromo-6-fluorophenyl, 4-(pyridin-3-yl)phenyl, 3-(pyridin-3-yl)phenyl, 4-(thiophen-2-yl)phenyl, 3-(thiophen-2-yl)phenyl, naphthyl, biphenyl-4-yl, 4'-fluorobiphenyl-4-yl, 4'-fluorobiphenyl-3-yl, 4'-chlorobiphenyl4-yl, 4'-chlorobiphenyl-3-yl, 4'-methoxybiphenyl4-yl, 4'-methoxybiphenyl-3-yl, (3',5'-dichloro)biphenyl-3-yl, 5-(4-fluorophenyl)-thiophen-2-yl, 5-(2-methoxyphenyl)-thiophen-2-yl, 5-(2-cyanophenyl)-thiophen-2-yl, 5-(2,5-dimethoxyphenyl)-thiophen-2-yl, 2-[2,2']bithiophenyl-5-yl, 5-(pyridin4-yl)-thiophen-2-yl, 5-(1H-indol-5-yl)-thiophen- 2-yl, 5-quinolin-8-yl-thiophen-2-yl or 5-(benzo[b]thiophen-2-yl)-thiophen-2-yl is particularly preferred for $R^4$.

$R^5$ is H or A, where A has a preferred meaning indicated beforehand.

$R^6$ is benzo[1,3]dioxol-5-yl.

$R^7$ is H, A, cycloalkyl or $(CH_2)_q$—$OR^5$, where A, cycloalkyl and $R^5$ have a preferred meaning beforehand and q is preferably 2 or 3.

Q is O or S, preferentially O.

Y is a direct bond, $(CH_2)_n$ or —$NR^5$—$(CH_2)_m$—, where $R^5$ has a preferred meaning indicated beforehand and n and mr have a preferred meaning indicated in the following. Y is preferentially a direct bond or $(CH_2)_n$, very particularly preferably a direct bond.

Z is phenylene, cyclohexylene, —$NR^5$—, O, —CH(OH)—, —$CA_2$- or

where $R^5$ and A have a preferred meaning indicated beforehand. Phenylene and/or cyclohexylene are particularly bonded in 1,4- or 1,3-position.

n is 1, 2, 3, 4, 5 or 6, preferentially 4.
m is 0, 1, 2, 3, 4, 5 or 6, preferentially 0, 1, 2 or 3.
o is 1, 2, 3, 4, 5, 6 or 7, preferentially 1, 2, 3 or 7.
p is 0, 1, 2, 3 or 4, preferentially 0, 1 or 2.
q is 1, 2, 3 or 4, preferentially 1, 2 or 3.

Some preferred groups of compounds can be expressed by the following subformulae Ia to In, which correspond to the formula I and in which the radicals not designated in greater detail have the meanings indicated in formula I, but in which in Ia R is H or OA and
$R^1$ is H, A, OA or Hal;
in Ib R is H or OA,
$R^1$ is H, A, OA or Hal and
Y is $(CH_2)_n$;
in Ic R is H or OA,
$R^1$ is H, A, OA or Hal,
$R^4$ is Ar,
Ar is unsubstituted phenyl and
Y is $(CH_2)_n$;
in Id R is H or OA,
$R^1$ is H, A, OA or Hal and
Y is a direct bond;
in Ie R is H or OA,
$R^1$ is H, A, OA or Hal and
Y is —$N(R^5)$—$(CH_2)_m$—;
in If R is H or OA,
$R^1$ is H, A, OA or Hal,
$R^4$ is Ar and
Y is a direct bond;
in Ig R is H or OA,
$R^1$ is H, A, OA or Hal,
$R^4$ Ar,
Ar is phenyl or biphenyl, which is unsubstituted or substituted by Hal, $Het^2$, OA or —$(CH_2)_p$—$N(R^7)_2$,
$R^7$ is H, A, cycloalkyl, $(CH_2)_3$—$OR^5$ or $(CH_2)_2$—$OR^5$ and
Y is a direct bond;
in Ih R is H,
$R^1$ is Hal,
$R^2$ is H,
$R^3$ is —$(CH_2)_o$-Het, —$(CHA)_p$-$(CH_2)_o$—$N(R^5)_2$ or —$(CH_2)_p$—$(CHA)_p$-$(CH_2)_m$—Ar, $R^4$ is Ar
Ar is unsubstituted phenyl and
Y is a direct bond;
in Ii R is H,
$R^1$ is Hal,
$R^2$ is H,
$R^3$ is —$(CH_2)_o$-Het, —$(CHA)_p$-$(CH_2)_o$—$N(R^5)_2$, —$(CH_2)_o$—$NR^5$-Het, —$(CH_2)_o$-Z-$(CH_2)_q$—$N(R^5)_2$ or —$(CH_2)_p$—$(CHA)_p$-$(CH_2)_m$—Ar,
$R^4$ is Ar,
Ar is biphenyl-4-yl and
Y is a direct bond;
in Ij R is H,
$R^1$ is Hal,
$R^2$ is H or A,
$R^3$ is A, cycloalkyl, -$Het^3$, —$(CH_2)_o$—$OR^5$, —$(CH_2)_o$—$OR^6$, —$(CH_2)_o$-Het, —$(CH_2)_o$—$NR^5$-Het, —$(CHA)_p$-$(CH_2)_o$—$N(R^5)_2$, —$(CH_2)_p$—$(CHA)_p$-$(CH_2)_m$—Ar, —$(CH_2)_o$-Z-$(CH_2)_q$—$N(R^5)_2$, or $NR^2R^3$ together form a saturated monocyclic heterocyclic radical having 5 to 6 ring members, where 1 or 2 N atoms are present and the heterocyclic radical can be mono- or disubstituted by OH, Ar, OAr or arylalkyl,
$R^4$ is Ar,
Ar is phenyl which is substituted by Br and
Y is a direct bond;
in Ik R is H,
$R^1$ is Hal,
$R^2$ is H,
$R^3$ is —$(CH_2)_o$-Het or —$(CHA)_p$-$(CH_2)_o$—$N(R^5)_2$,
$R^4$ is Ar,
Ar is phenyl or biphenyl, which is unsubstituted or substituted by Hal, $Het^2$, OA or —$(CH_2)_p$—$N(R^7)_2$,
$R^7$ is H, A, cycloalkyl, $(CH_2)_3$—$OR^5$ or $(CH_2)_2$—$OR^5$ and
Y is a direct bond;
in Im R is H,
$R^1$ is Hal,
$R^2$ is H,
$R^3$ is —$(CH_2)_o$-Het or —$(CHA)_p$-$(CH_2)_o$—$N(R^5)_2$,
$R^4$ is $Het^1$,
$Het^1$ is thiophen-2-yl, which is substituted by Ar or $Het^2$,
$R^7$ is H, A, cycloalkyl, $(CH_2)_3$—$OR^5$ or $(CH_2)_2$—$OR^5$ and
Y is a direct bond;
in In R is H,
$R^1$ is Hal,
$R^2$ is H,
$R^3$ is —$(CH_2)_o$-Het or —$(CHA)_p$-$(CH_2)_o$—$N(R^5)_2$,
$R^4$ is $Het^1$,
$Het^1$ is 5-(4-flour-phenyl)-thiophen-2-yl, 5-(2-methoxy-phenyl)-thiophen-2-yl, 5-(2-cyano-phenyl)-thiophen-2-yl, 5-(2,5-dimethoxy-phenyl)-thiophen-2-yl, 2-[2,2'] bithiophenyl-5-yl, 5-(1H-indol-5-yl)-thiophen-2-yl, 5-pyridine-4-yl-thiophen-2-yl, 5-quinolin-8-yl-thiophen-2-yl or 5-benzo[b]thiophen-2-yl-thiophen-2-yl $R^7$ is H, A, cycloalkyl, $(CH_2)_3$—$OR^5$ or $(CH_2)_2$—$OR^5$ and Y is a direct bond.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. In this case, use can also be made of variants which are known per se, but not mentioned here in greater detail.

The starting substances, if desired, can also be formed in situ such that they are not isolated from the reaction mixture, but immediately reacted further to give the compounds of the formula I.

The compounds of the formula I can be obtained by liberating them from their functional derivatives by solvolysis, in particular hydrolysis or by hydrogenolysis.

Preferred starting substances for the solvolysis or hydrogenolysis are those which otherwise correspond to the formula I, but instead of one or more free amino and/or hydroxyl groups contain corresponding protected amino and/or hydroxyl groups, in particular those which instead of an H—N— group carry an R'—N— group, in which R' is an amino protective group and/or those which instead of the H atom of a hydroxyl group carry a hydroxyl protective group, e.g. those which correspond to the formula I, but instead of a group —COOH carry a group —COOR", in which R" is a hydroxyl protective group.

A number of—identical or different—protected amino and/or hydroxyl groups can also be present in the molecule of the starting substance. If the protective groups present are different from one another, in many cases they can be removed selectively (lit.: T. W. Greene, P. G. M. Wuts, *Protective Groups in Organic Chemistry*, 2nd ed., Wiley, New York 1991 or P. J. Kocienski, *Protecting Groups*, 1st ed., Georg Thieme Verlag, Stuttgart-New-York, 1994).

The expression "amino protective group" is generally known and relates to groups which are suitable for protecting (for blocking) an amino group against chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1-20, in particular 1-8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and, in particular, alkoxycarbonyl groups, aryloxycarbonyl groups and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl (MOZ), 4-Nitro-benzyloxycarbonyl oder 9-fluorenylmethoxycarbonyl (Fmoc); 2-(phenylsulfonyl)ethoxycarbonyl; trimethylsilylethoxycarbonyl (Teoc) or arylsulfonyl such as 4-methoxy-2,3,6-trimethylphenyl-sulfonyl (Mtr). Preferred amino protective groups are BOC, furthermore CBZ, Fmoc, benzyl and acetyl; particularly preferred Fmoc.

The expression "hydroxyl protective group" is also generally known and relates to groups which are suitable for protecting a hydroxyl group against chemical reactions, but which are easily removable after the desired chemical reaction has been carried out at other positions in the molecule.

Typical groups of this type are the above mentioned unsubstituted or substituted aryl, aralkyl, aroyl or acyl groups, furthermore also alkylgroups, alkyl-, aryl- or aralkylsilylgroups or O,O— or O,S-acetals. The nature and size of the hydroxyl protective groups is not critical, since they are removed again after the desired chemical reaction or reaction sequence; groups having 1-20, in particular 1-10 C atoms, are preferred. Examples of hydroxyl protective groups are, inter alia, benzyl, 4-methoxybenzyl or 2,4-dimethoxybenzyl, aroyl groups such as benzoyl or p-nitrobenzoyl, acyl groups such as acetyl or pivaloyl, p-toluolsulfonyl, alkyl groups such as methyl or tert-butyl, but also allyl, alkylsilyl groups such as trimethylsilyl (TMS), triisopropylsilyl (TIPS), tert-butyidimethylsilyl (TBS) or triethylsilyl, trimethylsilylethyl, aralkylsilyl groups such as tert-butyidiphenylsilyl (TBDPS), cyclic acetals such as isopropylidene-, cyclopentylidene-, cyclohexylidene-, benzylidene-, p-methoxybenzylidene- or o,p-dimethoxybenzylideneacetal, acyclic acetales such as tetrahydropyranyl (Thp), methoxymethyl (MOM), methoxyethoxymethyl (MEM), benzyloxymethyl (BOM) or methylthiomethyl (MTM). Acetyl, benzyl, tert-butyl or TBS being particularly preferred.

The liberation of the compounds of the formula I from their functional derivatives depending on the protective group used is known in the present literature such as T. W. Greene, P. G. M. Wuts, *Protective Groups in Organic Chemistry*, 2nd ed., Wiley, New York 1991, P. J. Kocienski, *Protecting Groups*, 1st ed., Georg Thieme Verlag, Stuttgart-New-York, 1994. In this case, use can also be made of variants which are known per se, but not mentioned here in greater detail.

The groups BOC and O-tert-butyl can preferably be removed, for example, using TFA in dichloromethane or using approximately 3 to 5N HCl in dioxane at 15-30° C., the Fmoc group using an approximately 5 to 50% solution of dimethylamine, diethylamine or piperidine in DMF at 15-30° C.

Preferred starting substances for the solvolysis or hydrogenolysis includes also those which otherwise correspond to the formula I, but are attached to a solid phase. The liberation of the compounds of the formula I from the solid phase is known in the present literature such as Novabiochem—The Combinatorial Chemistry Catalog, March 99 and cited literature.

The solid phase with a carbonate moiety as terminal functional group can preferably be removed, for example, using TFA (50%) in dichloromethane.

The quinazolines of formula I can also preferably be prepared, using either solution or solid-phase techniques.

The term solid phase indicates a resin for solid-phase chemistry, especially for combinatorial chemistry, i.e. by robot- and computer-assisted syntheses, and subjected to mass screening as indicated in U.S. Pat. No. 5,463,564; M. A. Gallop et al., J. Med. Chem. 1994, 37, 1233-1251 and 1385-1401 and M. J. Sofia, Drug Discovery Today 1996, 1, 27-34). The polymeric material of the solid phase is generally chosen from the group consisting of cross-linked polystyrene, cross-linked polyacrylamide or other resins, natural polymers or silicagels.

The group of cross-linked polystyrene, cross-linked polyacrylamide or other resins includes e.g. polyacrylamide, polymethacrylamide, polyhydroxyethylmethacrylate, polyamide, polystyrene, (meth)acrylate copolymers, for instance from (methy)acrylic acid, esters of (meth)acrylic acid and/or 2-methylene-succinic acid, but-2-enoic acid or maleic acid, polyurethanes or other copolymers.

Suitable terminal functional groups or linkers on the surface of the resin have to be chosen to attach the compounds to the resin. There exists a variety of commercially available resins, e.g. in Novabiochem—The Combinatorial Chemistry-Catalog, March 99. Examples for suitable resins are carbonate resins with a modified carbonate group as terminal functional group like p-nitrophenylcarbonate resin, halogenated resins like Merrifield resin (chloromethylpolystyrene) or carboxy resins like carboxy polystyrene resin or NovaSyn® TG Carboxy Resin. p-Nitrophenylcarbonate resin is particularly preferred. These and other types of resins well known in the art can be used in the subject invention.

The quinazolines of formula I, in which Y is a direct bond or $(CH_2)_n$, can preferably be prepared by combining and reacting a 2-amino-benzonitrile of formula II with an aldehyde of formula III followed by converting the cyano group to an amide group, reacting the given formula IV with a base, chlorinating the given quinazolin-4-one of formula V and reacting the given formula VI with an amine of formula VII. The conversion of the cyano group to the amide group occurs by conventional means which are known to a skilled artisan. Particularly, the conversion occurs via oxidation within the presence of a base.

The quinazolines of formula I, in which Y is $—N(R^5)—(CH_2)_m—$, can be prepared by reacting a 2,4-dichloro-quinazoline of formula VIII with an amine of formula VII and reacting the given formula IX with an amine of formula X.

As a rule, the starting compounds of the formulae II, III, VII, VIII and X are known or commercially available.

The unknown compounds, however, can be prepared by methods known per se.

The 2,4-dichloro-quinazolines of formula II in which R and $R^1$ have a meaning indicated in claim 1 can be prepared by reacting a substituted anthranilic acid with KOCN/acetic acid in the presence of a base and chlorinating the given 1H-quinazoline-2,4-dione.

The aldehydes of formula III, as a rule, are also commercially available. Furthermore, syntheses for the preparation of aldehydes of formula III, such as, for example, the oxidation of an alcohol, can be used.

The amines of formula VII or X in which $R^2$, $R^3$, $NR^2R^3$, $R^5$, $R^4$ and m have a meaning indicated in claim 1, as a rule, are also commercially available and can be attached to the suitable resin or to a compound of formula VI, VIII or IX by coupling procedures well known in the art and as described in the ensuing Examples. Furthermore, syntheses for the preparation of amines of formula VII or X, such as, for example, the Gabriel synthesis, can be used.

For the preparation of compounds of the formula I in which $R^4$ is unsubstituted or substituted biphenyl, heteroarylsubstituted phenyl or aryl- or heteroaryl-substituted thiophenyl, an appropriate compound of the formula I in which $R^4$ is phenyl chloride, phenyl bromide, phenyl iodide, thiophenyl chloride, thiophenyl bromide or thiophenyl iodide can be reacted with the appropriate boronic acid derivatives in a Suzuki type coupling reaction. This reaction is expediently carried out under Palladium catalysis with different phosphines as coordination ligands, e.g. $Pd(P(Ph)_3)_2$, $Pd(II)Cl_2dppf$, $PdOAc_2+P(R^*)_3(R^*=phenyl$, cyclohexyl, tert-butyl) etc. in the presence of a base such as potassium carbonate, cesium carbonate, DBU, NaOH, in an inert solvent or solvent mixture, e.g. DMF or 1,4-dioxane at temperatures between 0° and 150°, preferably between 60° and 120°. Depending on the conditions used, the reaction time is between a few minutes and a number of days. The boronic acid derivatives can be prepared by conventional methods or are commercially available. The reactions can be carried out in analogy to the methods indicated in Suzuki et al., J. Am. Chem. Soc. 1989,111, 314ff., Suzuki et al., Chem. Rev. 1995, 95, 2457ff and G. C. Fu et al. Angew. Chem 1998, 110, 3586. The Suzuki type coupling reaction can be furthermore used to convert radicals R and $R^1$ into other radicals R and $R^1$, for e.g. to convert a halogen substituted quinazolines to a quinazoline substituted by substituted or unsubstituted phenyl.

For the preparation of compounds of the formula I in which R or $R^1$ is allyl, an appropriate compound of the formula I in which $R^4$ is quinazoline chloride, quinazoline bromide or quinazoline iodide can be reacted with allyltributyltin in a Stille type coupling reaction. This reaction is expediently carried out under Palladium catalysis with different phosphines as coordination ligands, e.g. $Pd(P(Ph)_3)_2$, $Pd(II)Cl_2dppf$, $PdOAc2+P(R^*)_3(R^*=phenyl$, cyclohexyl, tert-butyl) etc. in an inert solvent or solvent mixture, e.g. DMF or 1,4-dioxane at temperatures between 0° and 150°, preferably between 60° and 120°. Depending on the conditions used, the reaction time is between a few minutes and a number of days.

For the preparation of compounds of the formula I in which R or $R^1$ is $CH=CH—COOR^5$ or $CH=CH—CON(R^5)_2$, an appropriate compound of the formula I in which $R^4$ is quinazoline chloride, quinazoline bromide or quinazoline iodide can be reacted with substituted acrylate in a Heck type coupling reaction. This reaction is expediently carried out under Palladium catalysis with different phosphines as coordination ligands, e.g. $Pd(P(Ph)_3)_2$, $Pd(II)Cl_2dppf$, $PdOAc_2+P(R^*)_3(R^*=phenyl$, cyclohexyl, tert-butyl) etc. in the presence of a base such as triethyl amine or a catalyst tetrabutylammonium iodide, in an inert solvent or-solvent mixture, e.g. DMF or 1,4-dioxane at temperatures between 0° and 150°, preferably between 60° and 120°. Depending on the conditions used, the reaction time is between a few minutes and a number of days.

A base of the formula I can be converted into the associated acid addition salt using an acid, for example by reaction of equivalent amounts of the base and of the acid in an inert solvent such as ethanol and subsequent evaporation. Acids which give physiologically acceptable salts are particularly suitable for this reaction. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, p-toluenesulfonic acid, naphthalenemono- and disulfonic acids or laurylsulfuric acid. Salts with physiologically unacceptable acids, e.g. picrates, can be used for the isolation and/or purification of the compounds of the formula I.

On the other hand, compounds of the formula I with bases (e.g sodium or potassium hydroxide or carbonate) can be converted into the corresponding metal salts, in particular alkali metal or alkaline earth metal salts, or into the corresponding ammonium salts.

The invention furthermore relates to pharmaceutical preparations comprising at least one compound of the formula I and/or one of its physiologically acceptable salts, which are prepared, in particular, in an non-chemical way. In this case, the compounds of the formula I according to the invention can be brought into a suitable dose form together with at least one solid, liquid and/or semi-liquid excipient or auxiliary and, if appropriate, in combination with one or more other active compounds.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetate, gelatin, carbohydrates such as lactose or starch, magnesium stearate, talc and petroleum jelly. Tablets, pills, coated tablets, capsules, powders, granules, syrups, juices or drops are used, in particular, for oral administration, suppositories are used for rectal administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colorants, flavorings and/or one or more other active compounds, e.g. one or more vitamins.

The compounds of the formula I and their physiologically acceptable salts act as adhesion receptor antagonists, in particular glycoprotein 1bIX antagonists, and can be employed for the prophylaxis and/or therapy of thrombotic disorders and sequelae deriving therefrom. The disorders are acute coronary syndromes, angina pectoris, myocardial infarct, peripheral circulatory disorders, stroke, transient ischaemic attacks, arteriosclerosis and reocclusion/restenosis after angioplasty/stent implantation.

In this case, the substances according to the invention are as a rule administered in the dose of the glycoprotein IIbIIIa antagonist ReoPro® of preferably between approximately 1 and 500 mg, in particular between 5 and 100 mg, per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health and sex, on the diet, on the time and route of administration, and on the excretion rate, pharmaceutical combination and severity of the particular disorder to which the therapy applies. Oral administration is preferred.

Above and below, all temperatures are indicated in ° C. In the following examples, "customary working-up" for solution reactions means: if necessary, water is added, if necessary, depending on the constitution of the final product, the mixture is adjusted to pHs between 2 and 10 and extracted with ethyl acetate or dichloromethane, the organic phase is separated off, dried over sodium sulfate and evaporated, and the residue is purified by chromatography on silica gel and/or by crystallization.

"Customary working-up" for solid-phase reactions means: the crude reaction is filtered and washed with DMF twice, then sucessively with methanol and methylene chloride three times, and finally once with methyl tert-butyl ether. The resin is then dried in vacuo.

Mass spectrometry (MS) apparatuses Kratos OMIT and Finnigan LCQ. (M+H)$^+$ values or M$^+$ values are determined.

EXAMPLES

Example 1

1. Pyridine (0.144 mole) is given to a solution of 2-amino-4-chlorobenzonitrile (0,131 mole) in 100 ml tetrahydrofuran (THF) and a solution of 4-bromobenzoylchloride (31,6 g, 0,144 mole) in 50 ml THF is added under nitrogen. After addition of 100 ml THF, the mixture is stirred for 6 h at room temperature (rt). The crude reaction is then customary worked up for solution reactions affording 4-bromo-N-(5-chloro-2-cyano-phenyl)-benzamide as a solid; m.p. 151-152°.

MS calc.: 335,6. Found: 336, 338.

2. A suspension of 4-bromo-N-(5-chloro-2-cyano-phenyl)-benzamide (30 g, 89.4 mmol) in 500 ml methanol is mixed with 130 ml NaOH (2N) and perhydrite tablets [($H_2O_2$), 50 g]. The mixture is heated to boiling for 2 hrs. After cooling to rt and customary working up 4-bromo-N-(5-chloro-2-aminocarbonyl-phenyl)-benzamide is obtained as a solid; m.p. 172-173°.

MS calc.: 354. Found: 354.

3. 4-Bromo-N-(5-chloro-2-aminocarbonyl-phenyl)-benzamide (18.25 g, 51.6 mmol) is solved in 250 ml dioxane and 250 ml NaOH (1 N) are added. The mixture is heated to boiling for 5 days. After cooling to rt and customary working up 2-(4-bromo-phenyl)-7-chloro-3H-quinazolin-4-one is obtained as a solid; m.p. >300°.

MS calc.: 336. Found: 336.

4. 2-(4-Bromo-phenyl)-7-chloro-3H-quinazolin-4-one (38.7 mmol) is added to 50 ml thionylchloride and is heated at 40°. The mixture is treated with 6 ml dimethylformamide (DMF). After cooling to rt the mixture is stirred for 3 hrs. Customary working up gives 2-(4-bromo-phenyl)-4,7-dichloroquinazoline as a solid; m.p. 189-190°.

MS calc.: 354.0. Found: 355.

5. A solution of 2-(4-bromo-phenyl)-4,7-dichloroquinazoline (0.085 mmol, 30 mg) in 2 ml THF is treated with aniline (0.01 ml, 0.11 mmol). The suspension is heated to 60° and stirred for 18 hrs. The reaction mixture is filtered and the crystals are washed with THF and dried. [2-(4-Bromo-phenyl)-7-chloro-quinazolin-4-yl]-phenyl-amine is obtained.

MS calc.: 410.7. Found: 411.

Example 2

Analogously to example 1,1-(4-bromo-phenyl)-4,7-dichloro-quinazoline is reacted
with HNR$^2$R$^3$ to obtain compounds of formula I1

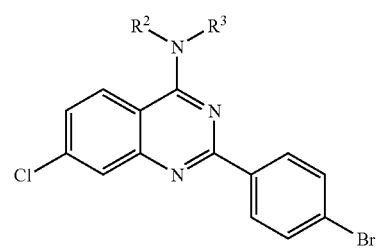

according to table 1.

TABLE 1

4-bromophenyl-quinazolines of formula I1

| R² in HNR²R³ and in I1 | R³ in HNR²R³ and in I1 | MS calc. | found |
|---|---|---|---|
| H | 1-(4-methylphenyl)-3-methyl-pyrazol-5(4H)-one | 506.8 | 507 |
| H | 2-(cyclopentyloxy)-methylphenyl | 494.8 | 495 |
| H | 4-(cyclopentyloxy)-methylphenyl | 494.8 | 495 |
| H | 3-(morpholinosulfonyl)-methylphenyl | 559.9 | 560 |
| H | 3-(N,N-diethylsulfamoyl)-methylphenyl | 545.9 | 546 |
| H | 3-(4,6-dimethoxypyrimidin-2-yl)-methylphenyl | 548.8 | 549 |
| H | 4-(4,6-dimethoxypyrimidin-2-yl)-methylphenyl | 548.8 | 550 |
| H | 5-methyl-isoquinolinyl | 461.8 | 463 |
| H | 4-morpholinophenyl-methyl | 495.8 | 496 |
| H | 2-ethyl-methylphenyl | 438.8 | 439 |
| H | 3-ethyl-methylphenyl | 438.8 | 439 |
| H | 4-ethyl-methylphenyl | 438.8 | 439 |
| H | 4-isopropyl-methylphenyl | 452.8 | 453 |
| H | 4-propyl-methylphenyl | 452.8 | 453 |
| H | 4-butyl-methylphenyl | 466.8 | 467 |
| H | 3-phenoxy-methylphenyl | 502.8 | 503 |
| H | 4-phenoxy-methylphenyl | 502.8 | 503 |
| H | 1-(methylsulfonyl)-5-methyl-indolinyl | 529.9 | 530 |

Example 3

A solution of 2-(4-bromo-phenyl)-4,7-dichloro-quinazoline (0.085 mmol, 30 mg) [prepared analogously to example 1] in 2 ml THF is treated with benzylamine (0.174 mmol, 0.019 ml). The mixture is heated at 60° for 6 hrs. After cooling to rt, the reaction mixture is filtered through a tentacle ion exchanger (LiChrolut® SCX: Merck ChromBook, 2nd ed. page 31). Evaporation of the solvent afforded benzyl-[2-(4-bromo-phenyl)-7-chloroquinazolin-4-yl]-amine.

MS calc.: 424.7. Found: 425.

Example 4

Analogously to example 3, 2-(4-bromo-phenyl)-4,7-dichloro-quinazoline is reacted with $HNR^2R^3$ to obtain compounds of formula I1

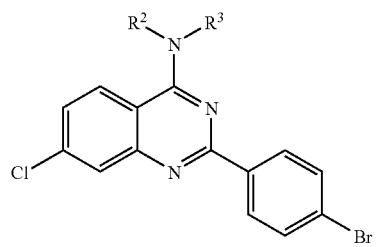

according to table 2.

TABLE 2

| 4-bromophenyl-quinazolines of formula I1 | | | |
|---|---|---|---|
| $R^2$ in $HNR^2R^3$ and in I1 | $R^3$ in $HNR^2R^3$ and in I1 | MS calc. | found |
| H | —CH$_2$—C$_6$H$_4$—CH$_3$ (4-) | 438.8 | 440 |
| H | —CH$_2$—C$_6$H$_4$—Cl (2-) | 459.2 | 460 |
| H | —CH$_2$—C$_6$H$_4$—F (2-) | 442.7 | 444 |
| H | —CH$_2$—C$_6$H$_4$—F (3-) | 442.7 | 444 |
| H | —CH$_2$—C$_6$H$_4$—F (4-) | 442.7 | 444 |
| H | —CH$_2$—C$_6$H$_4$—OCH$_3$ (2-) | 454.8 | 456 |
| H | —CH$_2$—C$_6$H$_3$(2-Cl)(3-CH$_3$) | 473.2 | 474 |
| H | —CH$_2$—C$_6$H$_3$(2-Cl)(4-Cl) | 493.6 | 494 |

TABLE 2-continued

4-bromophenyl-quinazolines of formula I1

| R² in HNR²R³ and in I1 | R³ in HNR²R³ and in I1 | MS calc. | found |
|---|---|---|---|
| H | —CH₂—(2,3-dichlorophenyl) | 493.6 | 494 |
| H | —CH₂—(4-chlorophenyl) | 459.2 | 460 |
| H | —CH₂—(4-methoxyphenyl) | 454.8 | 456 |
| H | —CH₂—(3,4-dimethoxyphenyl) | 484.8 | 486 |
| H | —CH₂—(benzo[1,3]dioxol-5-yl) | 468.7 | 470 |
| H | —CH(CH₃)—phenyl | 438.8 | 439 |
| H | —CH(CH₃)—(2-fluorophenyl) | 456.8 | 457 |
| H | —(CH₂)₂—O—(benzo[1,3]dioxol-5-yl) | 498.8 | 499 |
| H | —CH₂—(4'-fluorobiphenyl-3-yl) | 518.8 | 519 |
| H | —(CH₂)₂—CH(CH₃)—(2'-fluorobiphenyl-4-yl) | 560.9 | 561 |

TABLE 2-continued 4-bromophenyl-quinazolines of formula I1

| R² in HNR²R³ and in I1 | R³ in HNR²R³ and in I1 | MS calc. | found |
|---|---|---|---|
| H | —(CH₂)₂—CH(CH₃)—C₆H₄—C₆H₄—F (4-(4-fluorophenyl)phenyl, α-methyl) | 569.9 | 561 |
| H | —(CH₂)₂—CH(CH₃)—C₆H₄—C₆H₅ (4-phenylphenyl, α-methyl) | 542.9 | 543 |
| H | —(CH₂)₃—(imidazol-1-yl) | 442.8 | 444 |
| H | —(CH₂)₂—(benzo[1,3]dioxol-5-yl) | 482.8 | 483 |
| H | —(CH₂)₂—(3-methoxyphenyl) | 468.8 | 469 |
| H | —(CH₂)₂—(thiophen-2-yl) | 444.8 | 445 |
| H | —(CH₂)₂—(pyridin-4-yl) | 439.8 | 440 |
| H | —(CH₂)₂—(pyridin-2-yl) | 439.8 | 440 |
| H | —(CH₂)₃—(2-oxopyrrolidin-1-yl) | 459.8 | 460 |
| H | —(CH₂)₂—(morpholin-4-yl) | 447.8 | 449 |
| H | —(CH₂)₂—(piperidin-1-yl) | 445.8 | 447 |
| H | —(CH₂)₂—OCH₃ | 392.7 | 393 |
| H | —(CH₂)₂—N(CH₃)₂ | 405.7 | 405 |
| H | —(CH₂)₃—N(CH₃)₂ | 419.8 | 420 |
| H | —(CH₂)₂—N(Et)₂ | 433.8 | 434 |
| H | —(CH₂)₃—OCH₃ | 406.7 | 407 |
| H | —(CH₂)₃—N(CH₃)(CH₂CH(CH₃)₂) | 448.8 | 449 |

TABLE 2-continued 4-bromophenyl-quinazolines of formula I1

| $R^2$ in $HNR^2R^3$ and in I1 | $R^3$ in $HNR^2R^3$ and in I1 | MS calc. | found |
|---|---|---|---|
| H | —CH$_2$—(tetrahydrofuran-2-yl) | 418.7 | 419 |
| H | —(CH$_2$)$_3$—N(morpholine) | 461.8 | 462 |
| H | —(CH$_2$)$_2$—(octahydroindol-3-yl, N-CH$_3$) | 499.9 | 500 |
| H | Bu | 390.7 | 391 |
| H | Pentyl | 404.7 | 406 |
| H | —(CH$_2$)$_3$—N(4-methylpiperazin-1-yl)—CH$_3$ | 474.8 | 475 |

Example 5

Analogously to example 3, 2-(4-bromo-phenyl)-4-chloro-6-methylquinazoline is reacted
with 1-propyl-pyrrolidin-2-one to obtain
  1-{3-[2-(4-bromo-phenyl)-6-methyl-quinazolin-4-ylamino]-propyl}-pyrrolidin-2-one;
  MS calc.: 439.4. Found: 439.6;
with [2-(2-aminomethyl-phenylsulfanyl)-phenyl]-methanol to obtain
  [2-(2-{[2-(4-bromo-phenyl)-6-methyl-quinazolin-4-ylamino]-methyl}-phenylsulfanyl)-phenyl]-methanol;
  MS calc.: 542.5. Found: 544.2;

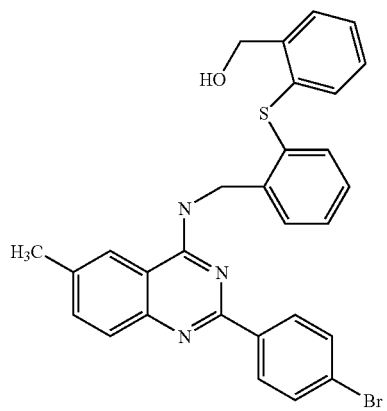

with 3-(2-methyl-piperidin-1-yl)-propylamine to obtain
  [2-(4-bromo-phenyl)-6-methyl-quinazolin-4-yl]-[3-(2-methyl-piperidin-1-yl)-propyl]-amine;
  MS calc.: 453.4. Found: 453.3;
with 2-pyridin-2-yl-ethylamine to obtain
  [2-(4-bromo-phenyl)-6-methyl-quinazolin-4-yl]-(2-pyridin-2-yl-ethyl)-amine;
  MS calc.: 419.3. Found: 419.3;
with 1-(3-trifluoromethyl-phenyl)-piperazine to obtain
  2-(4-bromo-phenyl)-6-methyl-4-[4-(3-trifluoromethyl-phenyl)-piperazin-1-yl]-quinazoline;
  MS calc.: 419.3. Found: 419.3;
with C-(1-ethyl-pyrrolidin-2-yl)-methylamine to obtain
  [2-(4-bromo-phenyl)-6-methyl-quinazolin-4-yl]-(1-ethyl-pyrrolidin-2-ylmethyl)-amine;
  MS calc.: 425.4. Found: 425.6;
with 4-benzyl-piperidin-4-ol to obtain
  4-benzyl-1-[2-(4-bromo-phenyl)-6-methyl-quinazolin-4-yl]-piperidin-4-ol;
  MS calc.: 488.4. Found: 490.3;
with 1-phenyl-piperazine to obtain
  2-(4-bromo-phenyl)-6-methyl-4-(4-phenyl-piperazin-1-yl)-quinazoline;
  MS calc.: 459.4. Found: 459.4;
with 3-morpholin-4-yl-propylamine to obtain
  [2-(4-bromo-phenyl)-6-methyl-quinazolin-4-yl]-(3-morpholin-4-yl-propyl)-amine;
  MS calc.: 441.4. Found: 441.3;
with 2-(1-methyl-pyrrolidin-2-yl)-ethylamine to obtain
  [2-(4-bromo-phenyl)-6-methyl-quinazolin-4-yl]-[2-(1-methyl-pyrrolidin-2-yl)-ethyl]-amine;
  MS calc.: 425.4. Found: 425.4;
with 3-(4-methyl-piperazin-1-yl)-propylamine to obtain
  [2-(4-bromo-phenyl)-6-methyl-quinazolin-4-yl]-[3-(4-methyl-piperazin-1-yl)-propyl]-amine;
  MS calc.: 454.4. Found: 454.4;
with 3,4,5-trimethoxy-benzylamine to obtain
  [2-(4-bromo-phenyl)-6-methyl-quinazolin-4-yl]-(3,4,5-trimethoxy-benzyl)-amine;
  MS calc.: 494.4. Found: 496.1;

with 2-flour-benzylamine to obtain
[2-(4-bromo-phenyl)-6-methyl-quinazolin-4-yl]-(2-flour-benzyl)-amine;
MS calc.: 422.3. Found: 422.4;
with benzyl-methyl-amine to obtain
benzyl-[2-(4-bromo-phenyl)-6-methyl-quinazolin-4-yl]-methyl-amine;
MS calc.: 418.2. Found: 418.4;
with methyl-(1-methyl-piperidin-4-ylmethyl)-amine to obtain
[2-(4-bromo-phenyl)-6-methyl-quinazolin-4-yl]-methyl-(1-methyl-piperidin-4-ylmethyl)-amine;
MS calc.: 425.3. Found: 425.2;
with cyclohexyl-methyl-amine to obtain
[2-(4-bromo-phenyl)-6-methyl-quinazolin4-yl]-cyclohexyl-methyl-amine;
MS calc.: 410.4. Found: 412.1;
with $N^1,N^1$-dimethyl-ethane-1,2-diamine to obtain
N'-[2-(4-bromo-phenyl)-6-methyl-quinazolin-4-yl]-N,N-dimethyl-ethane-1,2-diamine;
MS calc.: 385.3. Found: 386.3;
with butyl-methyl-amine to obtain
[2-(4-bromo-phenyl)-6-methyl-quinazolin-4-yl]-butyl-methyl-amine;
MS calc.: 384.3. Found: 384.4;
with N,N,N'-trimethyl-propane-1,3-diamine to obtain
N-[2-(4-bromo-phenyl)-6-methyl-quinazolin-4-yl]-N,N',N'-trimethyl-propane-1,3-diamine;
MS calc.: 413.4. Found: 415.2;
with 4-benzyl-piperidine to obtain
4-(4 benzyl-piperidin-1-yl)-2-(4-bromo-phenyl)-6-methyl-quinazoline;
MS calc.: 472.4. Found: 474.3;
with $N^1,N^1$-diethyl-pentane-1,4-diamine to obtain
$N^4$-[2-(4-bromo-phenyl)-6-methyl-quinazolin-4-yl]-$N^1$,$N^1$-diethyl-pentane-1,4-diamine;
MS calc.: 455.4. Found: 455.3;
with butylamine to obtain
[2-(4-bromo-phenyl)-6-methyl-quinazolin-4-yl]-butyl-amine;
with N,N-diethyl-propane-1,3-diamine to obtain
N'-[2-(4-bromo-phenyl)-6-methyl-quinazolin-4-yl]-N,N-diethyl-propane-1,3-diamine;
with benzylamine to obtain
benzyl-[2-(4-bromo-phenyl)-6-methyl-quinazolin-4-yl]-amine.

Example 6

Analogously to example 3, 2-(4-bromo-phenyl)-4,6-dichloro-quinazoline is reacted
with $N^1,N^1$-diethyl-pentane-1,4-diamine to obtain
$N^4$-[2-(4-bromo-phenyl)-6-chloro-quinazolin-4-yl]-$N^1$,$N^1$-diethyl-pentane-1,4-diamine;
MS calc.: 475.86. Found: 476;
with 4-benzyl-piperidine to obtain
4-(4-benzyl-piperidin-1-yl)-2-(4-bromo-phenyl)-6-chloro-quinazoline;
MS calc.: 492.84. Found: 493;
with N,N,N'-trimethyl-propane-1,3-diamine to obtain
N-[2-(4-bromo-phenyl)-6-chloro-quinazolin-4-yl]-N,N',N'-trimethyl-propane-1,3-diamine;
MS calc.: 433.78. Found: 434;
with butyl-methyl-amine to obtain
[2-(4-bromo-phenyl)-6-chloro-quinazolin-4-yl]-butyl-methyl-amine;
MS calc.: 404.74. Found: 405;
with $N^1,N^1$-dimethyl-ethane-1,2-diamine to obtain
N'-[2-(4-bromo-phenyl)-6-chloro-quinazolin-4-yl]-N,N-dimethyl-ethane-1,2-diamine;
with $N^1,N^1$-diethyl-ethane-1,2-diamine to obtain
N'-[2-(4-bromo-phenyl)-6-chloro-quinazolin-4-yl]-N,N-diethyl-ethane-1,2-diamine;
with cyclohexyl-methyl-amine to obtain
[2-(4-bromo-phenyl)-6-chloro-quinazolin-4-yl]-cyclohexyl-methyl-amine;
MS calc.: 430.77. Found: 431;
with methyl-(1-methyl-piperidin-4-ylmethyl)-amine to obtain
[2-(4-bromo-phenyl)-6-chloro-quinazolin-4-yl]-methyl-(1-methyl-piperidin-4-ylmethyl)-amine;
MS calc.: 445.79. Found: 446;
with benzyl-methyl-amine to obtain
benzyl-[2-(4-bromo-phenyl)-6-chloro-quinazolin-4-yl]-methyl-amine;
MS calc.: 438.75. Found: 439;
with 2-flour-benzylamine to obtain
[2-(4-bromo-phenyl)-6-chloro-quinazolin-4-yl]-(2-flour-benzyl)-amine;
MS calc.: 442.72. Found: 443;
with 3,4,5-trimethoxy-benzylamine to obtain
[2-(4-bromo-phenyl)-6-chloro-quinazolin-4-yl]-(3,4,5-trimethoxy-benzyl)-amine;
MS calc.: 514.80. Found: 515;
with 3-(4-methyl-piperazin-1-yl)-propylamine to obtain
[2-(4-bromo-phenyl)-6-chloro-quinazolin-4-yl]-[3-(4-methyl-piperazin-1-yl)-propyl]-amine;
MS calc.: 474.8 . Found: 474;
with 2-(1-methyl-pyrrolidin-2-yl)-ethylamine to obtain
[2-(4-bromo-phenyl)-6-chloro-quinazolin-4-yl]-[2-(1-methyl-pyrrolidin-2-yl)-ethyl]-amine;
MS calc.: 445.79. Found: 446;
with 3-morpholin-4-yl-propylamine to obtain
[2-(4-bromo-phenyl)-6-chloro-quinazolin-4-yl]-(3-morpholin-4-yl-propyl)-amine;
MS calc.: 461.78. Found: 462;
with 1-phenyl-piperazine to obtain
2-(4-bromo-phenyl)-6-chloro-4-(4-phenyl-piperazin-1-yl)-quinazoline;
MS calc.: 479.81. Found: 480;
with 4-benzyl-piperidin-4-ol to obtain
4-benzyl-1-[2-(4-bromo-phenyl)-6-chloro-quinazolin-4-yl]-piperidin-4-ol;
MS calc.: 508.84. Found: 509;
with C-(1-ethyl-pyrrolidin-2-yl)-methylamine to obtain
[2-(4-bromo-phenyl)-6-chloro-quinazolin-4-yl]-(1-ethyl-pyrrolidin-2-ylmethyl)-amine;
MS calc.: 445.78. Found: 446;
with 1-(3-trifluoromethyl-phenyl)-piperazine to obtain
2-(4-bromo-phenyl)-6-chloro-4-[4-(3-trifluoromethyl-phenyl)-piperazin-1-yl]-quinazoline;
MS calc.: 547.80. Found: 549;
with 2-pyridin-2-yl-ethylamine to obtain
[2-(4-bromo-phenyl)-6-chloro-quinazolin-4-yl]-(2-pyridin-2-yl-ethyl)-amine;
MS calc.: 439.74. Found: 440;
with 3-(2-methyl-piperidin-1-yl)-propylamine to obtain
[2-(4-bromo-phenyl)-6-chloro-quinazolin-4-yl]-[3-(2-methyl-piperidin-1-yl)-propyl]-amine;
MS calc.: 472.83. Found: 473;
with [2-(2-aminomethyl-phenylsulfanyl)-phenyl]-methanol to obtain
[2-(2-{[2-(4-bromo-phenyl)-6-chloro-quinazolin-4-ylamino]-methyl}-phenylsulfanyl)-phenyl]-methanol;

MS calc.: 562.92. Found: 563;
with 1-propyl-pyrrolidin-2-one to obtain
1-{3-[2-(4-bromo-phenyl)-6-chloro-quinazolin-4-ylamino]-propyl}-pyrrolidin-2-one;
MS calc.: 459.77. Found: 460;
with butylamine to obtain
[2-(4-bromo-phenyl)-6-chloro-quinazolin-4-yl]-butyl-amine;
with N,N-diethyl-propane-1,3-diamine to obtain
N'-[2-(4-bromo-phenyl)-6-chloro-quinazolin-4-yl]-N,N-diethyl-propane-1,3-diamine;
with benzylamine to obtain
benzyl-[2-(4-bromo-phenyl)-6-chloro-quinazolin-4-yl]-amine.

Example 7

Analogously to example 3, 2-(4-bromo-phenyl)-4-chloro-6,7-dimethoxy-quinazoline is reacted
with 1-propyl-pyrrolidin-2-one to obtain
1-{3-[2-(4-bromo-phenyl)-6,7-dimethoxy-quinazolin-4-ylamino]-propyl}-pyrrolidin-2-one;
with [2-(2-aminomethyl-phenylsulfanyl)-phenyl]-methanol to obtain
[2-(2-{[2-(4-bromo-phenyl)-6,7-dimethoxy-quinazolin-4-ylamino]-methyl}-phenylsulfanyl)-phenyl]-methanol;
MS calc.: 588.52. Found: 589;
with 3-(2-methyl-piperidin-1-yl)-propylamine to obtain
[2-(4-bromo-phenyl)-6,7-dimethoxy-quinazolin-4-yl]-[3-(2-methyl-piperidin-1-yl)-propyl]-amine;
MS calc.: 499.45. Found: 500;
with 2-pyridin-2-yl-ethylamine to obtain
[2-(4-bromo-phenyl)-6,7-dimethoxy-quinazolin-4-yl]-(2-pyridin-2-yl-ethyl)-amine;
MS calc.: 465.35. Found: 466;
with 1-(3-trifluoromethyl-phenyl)-piperazine to obtain
2-(4-bromo-phenyl)-6,7-dimethoxy-4-[4-(3-trifluoromethyl-phenyl)-piperazin-1-yl]-quinazoline;
MS calc.: 573.41. Found: 574;
with C-(1-ethyl-pyrrolidin-2-yl)-methylamine to obtain
[2-(4-bromo-phenyl)-6,7-dimethoxy-quinazolin-4-yl]-(1-ethyl-pyrrolidin-2-ylmethyl)-amine;
MS calc.: 483.41. Found: 484;
with 4-benzyl-piperidin-4-ol to obtain
4-benzyl-1-[2-(4-bromo-phenyl)-6,7-dimethoxy-quinazolin-4-yl]-piperidin-4-ol;
MS calc.: 534.45. Found: 535;
with 1-phenyl-piperazine to obtain
2-(4-bromo-phenyl)-6,7-dimethoxy-4-(4-phenyl-piperazin-1-yl)-quinazoline;
MS calc.: 505.41. Found: 506;
with 3-morpholin-4-yl-propylamine to obtain
[2-(4-bromo-phenyl)-6,7-dimethoxy-quinazolin-4-yl]-(3-morpholin-4-yl-propyl)-amine;
MS calc.: 487.39. Found: 488;
with 2-(1-methyl-pyrrolidin-2-yl)-ethylamine to obtain
[2-(4-bromo-phenyl)-6,7-dimethoxy-quinazolin-4-yl]-[2-(1-methyl-pyrrolidin-2-yl)-ethyl]-amine;
MS calc.: 471.39. Found: 472;
with 3-(4-methyl-piperazin-1-yl)-propylamine to obtain
[2-(4-bromo-phenyl)-6,7-dimethoxy-quinazolin-4-yl]-[3-(4-methyl-piperazin-1-yl)-propyl]-amine;
MS calc.: 486.43. Found: 487;
with 3,4,5-trimethoxy-benzylamine to obtain
[2-(4-bromo-phenyl)-6,7-dimethoxy-quinazolin-4-yl]-(3,4,5-trimethoxy-benzyl)-amine;
MS calc.: 540.41. Found: 541;
with 2-flour-benzylamine to obtain
[2-(4-bromo-phenyl)-6,7-dimethoxy-quinazolin-4-yl]-(2-flour-benzyl)-amine;
MS calc.: 468.32. Found: 469;
with benzyl-methyl-amine to obtain
benzyl-[2-(4-bromo-phenyl)-6,7-dimethoxy-quinazolin-4-yl]-methyl-amine;
MS calc.: 464.36. Found: 465;
with methyl-(1-methyl-piperidin-4-ylmethyl)-amine to obtain
[2-(4-bromo-phenyl)-6,7-dimethoxy-quinazolin-4-yl]-methyl-(1-methyl-piperidin-4-ylmethyl)-amine;
MS calc.: 471.40. Found: 472;
with cyclohexyl-methyl-amine to obtain
[2-(4-bromo-phenyl)-6,7-dimethoxy-quinazolin-4-yl]-cyclohexyl-methyl-amine;
MS calc.: 456.38. Found: 457;
with $N^1,N^1$-dimethyl-ethane-1,2-diamine to obtain
N'-[2-(4-bromo-phenyl)-6,7-dimethoxy-quinazolin-4-yl]-N,N-dimethyl-ethane-1,2-diamine;
MS calc.: 431.33. Found: 432;
with $N^1,N^1$-diethyl-ethane-1,2-diamine to obtain
N'-[2-(4-bromo-phenyl)-6,7-dimethoxy-quinazolin-4-yl]-N,N-diethyl-ethane-1,2-diamine;
with butyl-methyl-amine to obtain
[2-(4-bromo-phenyl)-6,7-dimethoxy-quinazolin-4-yl]-butyl-methyl-amine;
MS calc.: 431.35. Found: 432;
with N,N,N'-trimethyl-propane-1,3-diamine to obtain
N-[2-(4-bromo-phenyl)-6,7-dimethoxy-quinazolin-4-yl]-N,N',N'-trimethyl-propane-1,3-diamine;
MS calc.: 459.38. Found: 460;
with 4-benzyl-piperidine to obtain
4-(4-benzyl-piperidin-1-yl)-2-(4-bromo-phenyl)-6,7-dimethoxy-quinazoline;
MS calc.: 518.45. Found: 519;
with $N^1,N^1$-diethyl-pentane-1,4-diamine to obtain
$N^4$-[2-(4-bromo-phenyl)-6,7-dimethoxy-quinazolin-4-yl]-$N^1,N^1$-diethyl-pentane-1,4-diamine;
MS calc.: 501.47. Found: 502;
with butylamine to obtain
[2-(4-bromo-phenyl)-6,7-dimethoxy-quinazolin-4-yl]-butyl-amine;
with N,N-diethyl-propane-1,3-diamine to obtain
N'-[2-(4-bromo-phenyl)-6,7-dimethoxy-quinazolin-4-yl]-N,N-diethyl-propane-1,3-diamine;
with benzylamine to obtain
benzyl-[2-(4-bromo-phenyl)-6,7-dimethoxy-quinazolin-4-yl]-amine.

Example 8

Analogously to example 3, 2-phenyl-4,7-dichloro-quinazoline [prepared analogously to example 1, starting compounds 2-amino-4-chlorobenzonitrile and benzoylchloride] is reacted
with 3-imidazol-1-yl-propylamine to obtain
(7-chloro-2-phenyl-quinazolin-4-yl)-(3-imidazol-1-yl-propyl)-amine;
with $N^1,N^1$-diethyl-pentane-1,4-diamine to obtain
$N^4$-(7-chloro-2-phenyl-quinazolin-4-yl)-$N^1$, $N^1$-diethyl-pentane-1,4-diamine;
with 3-morpholin-4-yl-propylamine to obtain
(7-chloro-2-phenyl-quinazolin-4-yl)-(3-morpholin-4-yl-propyl)-amine;

with phenyl-amine to obtain
(7-chloro-2-phenyl-quinazolin-4-yl)-phenyl-amine.

Analogously to example 3, N-[4-(4,7-dichloro-quinazolin-2-yl)-phenyl]-3-methyl-butyramide [prepared analogously to example 1, starting compounds 2-amino-4-chlorobenzonitrile and 4-(3-methyl-butyrylamino)-benzoyl chloride] is reacted
with $N^1,N^1$-diethyl-propane-1,3-diamine to obtain
N-{4-[7-chloro-4-(3-diethylamino-propylamino)-quinazolin-2-yl]-phenyl}-3-methyl-butyramide.

Example 9

Analogously to example 3, 2-biphenyl-4-yl-4,7-dichloro-quinazoline [prepared analogously to example 1, starting compounds 2-amino-4-chlorobenzonitrile and biphenyl-4-carbonyl chloride] is reacted
with $N^1,N^1$-diethyl-pentane-1,4-diamine to obtain
$N^4$-(2-biphenyl-4-yl-7-chloro-quinazolin-4-yl)-$N^1,N^1$-diethyl-pentane-1,4-diamine;
with 3-imidazol-1-yl-propylamine to obtain
(2-biphenyl-4-yl-7-chloro-quinazolin-4-yl)-(3-imidazol-1-yl-propyl)-amine;
with $N^1,N^1$-diethyl-ethane-1,2-diamine to obtain
N'-(2-biphenyl-4-yl-7-chloro-quinazolin-4-yl)-N, N-diethyl-ethane-1,2-diamine;
with $N^1,N^1$-diethyl-propane-1,3-diamine to obtain
N'-(2-biphenyl-4-yl-7-chloro-quinazolin-4-yl)-N, N-diethyl-propane-1,3-diamine;
with 3-morpholin-4-yl-propylamine to obtain
(2-biphenyl-4-yl-7-chloro-quinazolin-4-yl)-(3-morpholin-4-yl-propyl)-amine;
with 1-(3-amino-propyl)-pyrrolidin-2-one to obtain
1-[3-(2-biphenyl-4-yl-7chloro-quinazolin-4-ylamino)-propyl]-pyrrolidin-2-one;
with 4-(2-amino-ethyl)-phenylamine to obtain
[2-(4-amino-phenyl)-ethyl]-(2-biphenyl-4-yl-7-chloro-quinazolin-4-yl)-amine;
with $N^1$-(5-nitro-pyridin-2-yl)-ethane-1,2-diamine to obtain
N-(2-biphenyl-4-yl-7-chloro-quinazolin-4-yl)-N'-(5-nitro-pyridin-2-yl)-ethane-1,2-diamine;
with 2-piperazin-1-yl-ethylamine to obtain
(2-biphenyl-4-yl-7-chloro-quinazolin-4-yl)-(2-piperazin-1-yl-ethyl)-amine;
with (4-aminomethyl-phenyl)-dimethyl-amine to obtain
(2-biphenyl-4-yl-7-chloro-quinazolin-4-yl)-(4-dimethylamino-benzyl)-amine;
with 2-pyridin-2-yl-ethylamine to obtain
(2-biphenyl-4-yl-7-chloro-quinazolin-4-yl)-(2-pyridin-2-yl-ethyl)-amine;
with C-(3-aminomethyl-cyclohexyl)-methylamine to obtain
(3-aminomethyl-cyclohexylmethyl)-(2-biphenyl-4-yl-7-chloro-quinazolin-4-yl)-amine;
with heptane-1,7-diamine to obtain
$N^1$-(2-biphenyl-4-yl-7-chloro-quinazolin-4-yl)-heptane-1,7-diamine;
with propane-1,3-diamine to obtain
$N^1$-(2-biphenyl-4-yl-7-chloro-quinazolin-4-yl)-propane-1,3-diamine.

Example 10

Analogously to example 3, 2-(4-bromo-phenyl)-4,7-dichloro-quinazoline [prepared analogously to example 1, starting compounds 2-amino-4-chlorobenzonitrile and 4-bromobenzoylchloride] is reacted with $N^1,N^1$-diethyl-propane-1,3-diamine to obtain
N'-[2-(4-bromo-phenyl)-7-chloro-quinazolin-4-yl]-N,N-diethyl-propane-1,3-diamine.

1,2 Equivalents of $K_2CO_3$, 1,2 equivalents of 4-chlorophenylboronic acid and 10 mol % of $Pd((PPh_3)_4$ are added to a solution of N'-[2-(4-bromo-phenyl)-7-chloro-quinazolin4-yl]-N,N-diethyl-propane-1,3-diamine (16,5 mmol) in 80 ml of DMF and it is heated at 80° until conversion is complete. After filtering off the catalyst and customary working up for solution reactions, N'-[7-chloro-2-(4'-chloro-biphenyl-4-yl)-quinazolin-4-yl]-N,N-diethyl-propane-1,3-diamine is obtained.

Example 11

Analogously to example 10, N'-[2-(4-bromo-phenyl)-7-chloro-quinazolin-4-yl]-N,N-diethyl-propane-1,3-diamine is reacted
with 4-methoxyphenylboronic acid to obtain
N'-[7-chloro-2-(4'-methoxy-biphenyl-4-yl)-quinazolin-4-yl]-N,N-diethyl-propane-1,3-diamine;
with 3-acetylaminophenylboronic acid to obtain
N-{4'-[7-chloro-4-(3-diethylamino-propylamino)-quinazolin-2-yl]-biphenyl-3-yl}-acetamide;
with 3-formylphenylboronic acid to obtain
4'-[7-chloro-4-(3-diethylamino-propylamino)-quinazolin-2-yl]-biphenyl-3-carbaldehyde;
with 4-[(cyclohexylmethyl-amino)-methyl]-phenylboronic acid to obtain
N-(7-chloro-2-{4'-[(cyclohexylmethyl-amino)-methyl]-biphenyl-4-yl}-quinazolin-4-yl)-N', N'-diethyl-propane-1,3-diamine.

Analogously to example 10, N'-[2-(3-bromo-phenyl)-7-chloro-quinazolin-4-yl]-N,N-diethyl-propane-1,3-diamine is reacted
with 3,5-dichlorophenylboronic acid to obtain
N'-[7-chloro-2-(3',5'-dichloro-biphenyl-3-yl)-quinazolin-4-yl]-N,N-diethyl-propane-1,3-diamine;
with 4-fluorophenylboronic acid to obtain
N'-[7-chloro-2-(4'-fluoro-biphenyl-3-yl)-quinazolin-4-yl]-N,N-diethyl-propane-1,3-diamine.

Example 12

Analogously to example 10, $N^4$-[2-(4-bromo-phenyl)-7-chloro-quinazolin-4-yl]-$N^1,N^1$-diethyl-pentane-1,4-diamine (prepared according to example 3) is reacted
with 4-chlorophenylboronic acid to obtain
$N^4$-[7-chloro-2-(4'-chloro-biphenyl-4-yl)-quinazolin-4-yl]-$N^1,N^1$-diethyl-pentane-1,4-diamine;
with 3-formylphenylboronic acid to obtain
4'-[7-chloro-4-(4-diethylamino-1-methyl-butylamino)-quinazolin-2-yl]-biphenyl-3-carbaldehyde;
with 3-[(hydroxypropyl-amino)-methyl]-phenylboronic acid to obtain
3-({4'-[7-chloro-4-(4-diethylamino-1-methyl-butylamino)-quinazolin-2-yl]-biphenyl-3-ylmethyl}-amino)-propan-1-ol.

Analogously to example 10, $N^4$-[2-(3-bromo-phenyl)-7-chloro-quinazolin-4-yl]-$N^1,N^1$-diethyl-pentane-1,4-diamine is reacted
with 4-methoxyphenylboronic acid to obtain
$N^4$-[7-chloro-2-(4'-methoxy-biphenyl-3-yl)-quinazolin-4-yl]-$N^1$,$N^1$-diethyl-pentane-1,4-diamine;

with (pyridin-3-yl)boronic acid to obtain
N⁴-[7-chloro-2-(3-pyridin-3-yl-phenyl)-quinazolin-4-yl]-N¹,N¹-diethyl-pentane-1,4-diamine.

Example 13

Analogously to example 3, 2-(4-bromo-phenyl)-4,7-dichloro-quinazoline [prepared analogously to example 1, starting compounds 2-amino-4-chlorobenzonitrile and 4-bromobenzoylchloride] is reacted with 2-(1-methyl-octahydro-indol-3-yl)-ethylamine to obtain
[2-(4-bromo-phenyl)-7-chloro-quinazolin-4-yl]-[2-(1-methyl-octahydro-indol-3-yl)-ethyl]-amine.
Analogously to example 10, [2-(4-bromo-phenyl)-7-chloro-quinazolin-4-yl]-[2-(1-methyl-octahydro-indol-3-yl)-ethyl]-amine is reacted
with 4-fluorophenylboronic acid to obtain
[7-chloro-2-(4'-fluoro-biphenyl-4-yl)-quinazolin-4-yl]-[2-(1-methyl-octahydro-indol-3-yl)-ethyl]-amine;
with (thiophen-2-yl)boronic acid to obtain
[7-chloro-2-(4-thiophen-2-yl-phenyl)-quinazolin-4-yl]-[2-(1-methyl-octahydro-indol-3-yl)-ethyl]-amine;
with (pyridin-3-yl)boronic acid to obtain
[7-chloro-2-(4-pyridin-3-yl-phenyl)-quinazolin-4-yl]-[2-(1-methyl-octahydro-indol-3-yl)-ethyl]-amine.
Analogously to example 10, [2-(3-bromo-phenyl)-7-chloro-quinazolin-4-yl]-[2-(1-methyl-octahydro-indol-3-yl)-ethyl]-amine is reacted
with (thiophen-2-yl)boronic acid to obtain
[7-chloro-2-(3-thiophen-2-yl-phenyl)-quinazolin-4-yl]-[2-(1-methyl-octahydro-indol-3-yl)-ethyl]-amine;
with 3-(acetylamino)-phenylboronic acid to obtain
N-(3'-{7-chloro-4-[2-(1-methyl-octahydro-indol-3-yl)-ethylamino]-quinazolin-2-yl}-biphenyl-3-yl)-formamide.

Example 14

Analogously to example 3, 2-(4-bromo-phenyl)-4,7-dichloro-quinazoline [prepared analogously to example 1, starting compounds 2-amino-4-chlorobenzonitrile and 4-bromobenzoylchloride] is reacted with 2-(1-methyl-piperidin-3-yl)-ethylamine to obtain
[7-chloro-2-(4-bromo-phenyl)-quinazolin-4-yl]-[2-(1-methyl-piperidin-3-yl)-ethyl]-amine.
Analogously to example 10, [7-chloro-2-(4-bromo-phenyl)-quinazolin-4-yl]-[2-(1-methyl-piperidin-3-yl)-ethyl]-amine is reacted
with 3-formylphenylboronic acid to obtain
4'-{7-chloro-4-[2-(1-methyl-piperidin-3-yl)-ethylamino]-quinazolin-2-yl}-biphenyl-3-carbaldehyde;
with (thiophen-3-yl)boronic acid to obtain
[7-chloro-2-(4-thiophen-3-yl-phenyl)-quinazolin-4-yl]-[2-(1-methyl-piperidin-3-yl)-ethyl]-amine;
with 2-(formyl-thiophen-3-yl)boronic acid to obtain
3-(4-{7-chloro-4-[2-( 1-methyl-piperidin-3-yl)-ethylamino]-quinazolin-2-yl]-phenyl}-thiophene-2-carbaldehyde;
with 3-[(2-methoxy-ethylamino)-methyl]-phenylboronic acid to obtain
(7-chloro-2-{3'-[(2-methoxy-ethylamino)-methyl]-biphenyl-4-yl}-quinazolin-4-yl)-[2-(1-methyl-piperidin-3-yl)-ethyl]-amine;
with {2-[1-(methoxycarbonylmethyl-amino)-ethyl]-thiophen-3-yl}-boronic acid to obtain
{1-[3-(4-{7-chloro-4-[2-(1-methyl-piperidin-3-yl)-ethylamino]-quinazolin-2-yl}-phenyl)-thiophen-2-yl]-ethylamino}-acetic acid methyl ester

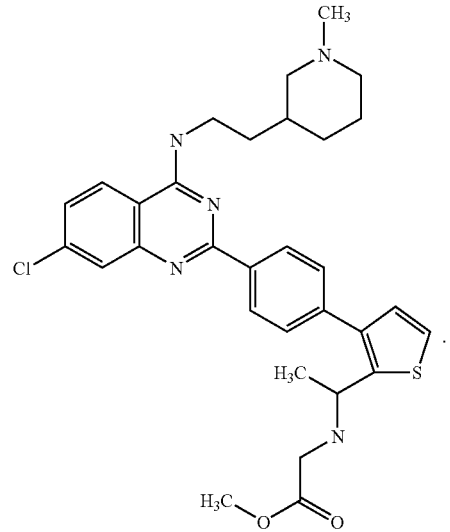

Analogously to example 3, 2-(4-bromo-phenyl)-4,7-dichloro-quinazoline [prepared analogously to example 1] is reacted with 2-morpholin-4-yl-ethylamine to obtain
[2-(4-bromo-phenyl)-7-chloro-quinazolin-4-yl]-(2-morpholin-4-yl-ethyl)-amine.
Analogously to example 10, [2-(4-bromo-phenyl)-7-chloro-quinazolin-4-yl]-(2-morpholin-4-yl-ethyl)-amine is reacted
with 3,4-dimethoxyphenylboronic acid to obtain
[7-chloro-2-(3',4'-dimethoxy-biphenyl-4-yl)-quinazolin-4-yl]-(2-morpholin-4-yl-ethyl)-amine;
with 4-formylphenylboronic acid to obtain
4'-[7-chloro-4-(2-morpholin-4-yl-ethylamino)-quinazolin-2-yl]-biphenyl-4-carbaldehyde;
with 2-(formyl-thiophen-3-yl)boronic acid to obtain
3-{4-[7-chloro-4-(2-morpholin-4-yl-ethylamino)-quinazolin-2-yl]-phenyl}-thiophene-2-carbaldehyde;
with 4-(propylaminomethyl)-phenylboronic acid to obtain
[7-chloro-2-(4'-propylaminomethyl-biphenyl-4-yl)-quinazolin-4-yl]-(2-morpholin-4-yl-ethyl)-amine.

Example 15

Analogously to example 3, 2-(5-bromo-thiophen-2-yl)-4,7-dichloro-quinazoline [prepared analogously to example 1, starting compounds 2-amino-4-chlorobenzonitrile and 5-bromo-thiophene-2-carbonyl chloride] is reacted with 2-(1-methyl-octahydro-indol-3-yl)-ethylamine to obtain
[2-(5-bromo-thiophen-2-yl)-7-chloro-quinazolin-4-yl]-[2-(1-methyl-octahydro-indol-3-yl)-ethyl]-amine.
Analogously to example 10, [2-(5-bromo-thiophen-2-yl)-7-chloro-quinazolin-4-yl]-[2-(1-methyl-octahydro-indol-3-yl)-ethyl]-amine is reacted
with 4-fluorophenylboronic acid to obtain
{7-chloro-2-[5-(4-fluoro-phenyl)-thiophen-2-yl]-quinazolin-4-yl}-[2-(1-methyl-octahydro-indol-3-yl)-ethyl]-amine;
with 2-methoxyphenylboronic acid to obtain
{7-chloro-2-[5-(2-methoxy-phenyl)-thiophen-2-yl]-quinazolin-4-yl}-[2-(1-methyl-octahydro-indol-3-yl)-ethyl]-amine;

with (1H-indol-5-yl)boronic acid to obtain
{7-chloro-2-[5-(1H-indol-5-yl)-thiophen-2-yl]-quinazolin-4-yl}-[2-(1-methyl-octahydro-indol-3-yl)-ethyl]-amine;
with (quinolin-8-yl)boronic acid to obtain
[7-chloro-2-(5-quinolin-8-yl-thiophen-2-yl)-quinazolin-4-yl]-[2-(1-methyl-octahydro-indol-3-yl)-ethyl]-amine.

Analogously to example 3, 2-(5-bromo-thiophen-2-yl)-4,7-dichloro-quinazoline [prepared analogously to example 1] is reacted with $N^1,N^1$-diethyl-propane-1,3-diamine to obtain
N'-[2-(5-bromo-thiophen-2-yl)-7-chloro-quinazolin-4-yl]-N,N-diethyl-propane-1,3-diamine.

Analogously to example 10, N'-[2-(5-bromo-thiophen-2-yl)-7-chloro-quinazolin-4-yl]-N,N-diethyl-propane-1,3-diamine is reacted
with (thiophen-2-yl)boronic acid to obtain
N'-(2-[2,2']bithiophenyl-5-yl-7-chloro-quinazolin-4-yl)-N,N-diethyl-propane-1,3-diamine;
with (pyridin-4-yl)boronic acid to obtain
N'-[7-chloro-2-(5-pyridin-4-yl-thiophen-2-yl)-quinazolin-4-yl]-N,N-diethyl-propane-1,3-diamine;
with (2,5-dimethoxy)phenylboronic acid to obtain
N'-{7-chloro-2-[5-(2,5-dimethoxy-phenyl)-thiophen-2-yl]-quinazolin-4-yl}-N,N-diethyl-propane-1,3-diamine.

Analogously to example 3, 2-(5-bromo-thiophen-2-yl)-4,7-dichloro-quinazoline [prepared analogously to example 1] is reacted with $N^1,N^1$-diethyl-pentane-1,4-diamine to obtain
$N^4$-[2-(5-bromo-thiophen-2-yl)-7-chloro-quinazolin-4-yl]-$N^1,N^1$-diethyl-pentane-1,4-diamine.

Analogously to example 10, $N^4$-[2-(5-bromo-thiophen-2-yl)-7-chloro-quinazolin-4-yl]-N',N'-diethyl-pentane-1,4-diamine is reacted
with 2-cyanophenylboronic acid to obtain
2-{5-[7-chloro-4-(4-diethylamino-1-methyl-butylamino)-quinazolin-2-yl]-thiophen-2-yl}-benzonitrile;
with (benzo[b]thiophen-2-yl)boronic acid to obtain
$N^4$-[2-(5-benzo[b]thiophen-2-yl-thiophen-2-yl)-7-chloro-quinazolin-4-yl]-$N^1,N^1$-diethyl-pentane-1,4-diamine.

Example 16

Analogously to example 3, 4-chloro-2-(4-phenyl-butyl)-quinazoline [prepared analogously to example 1, starting compounds 2-amino-benzonitrile and 5-phenyl-pentanoyl chloride] is reacted
with $N^1,N^1$-diethyl-pentane-1,4-diamine to obtain
$N^1$,$N^1$-diethyl-$N^4$-[2-(4-phenyl-butyl)-quinazolin-4-yl]-pentane-1,4-diamine;

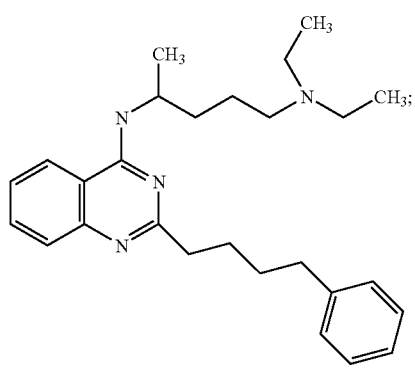

with C-(3-aminomethyl-cyclohexyl)-methylamine to obtain
(3-aminomethyl-cyclohexylmethyl)-[2-(4-phenyl-butyl)-quinazolin-4-yl]-amine;
MS calc.: 402.6 . Found: 403.6.

Example 17

1. A solution of 2,4,7-trichloro-quinazoline (38.7 mmol) in 50 ml DMF is treated with $N^1,N^1$-diethyl-pentane-1,4-diamine (50 mmol). The mixture is stirred at rt for 4 hrs. A solution of C-(5-methoxy-1H-indol-3-yl)-methylamine (50 mmol) in 10 ml DMF is added and the mixture is heated to 80-100° for 3 days. Customary working up gives 7-chloro-$N^4$-(4-diethylamino-1-methyl-butyl)-$N^2$-(5-methoxy-1H-indol-3-ylmethyl)-quinazoline-2,4-diamine

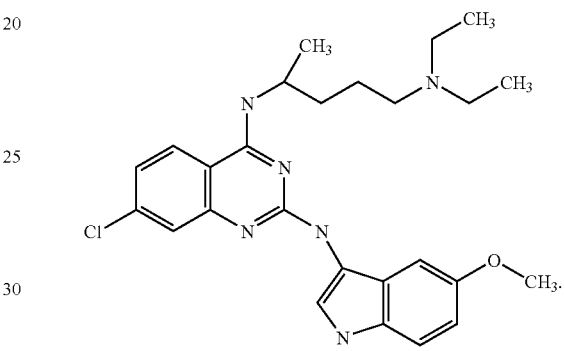

Analogously to example 17, 2,4,7-trichloro-quinazoline is reacted with $N^1,N^1$-diethyl-pentane-1,4-diamine to give $N^4$-(2,7-dichloro-quinazolin-4-yl)-$N^1,N^1$-diethyl-pentane-1,4-diamine and is further reacted
with 5-bromo-2-fluoro-benzylamine to obtain
$N^2$-(5-bromo-2-fluoro-benzyl)-7-chloro-$N^4$-(4-diethylamino-1-methyl-butyl)-quinazoline-2,4-diamine;
with 3,5-bis-trifluoromethyl-benzylamine to obtain
$N^2$-(3,5-bis-trifluoromethyl-benzyl)-7-chloro-$N^4$-(4-diethylamino-1-methyl-butyl)-quinazoline-2,4-diamine;
with 4-tert-butyl-benzylamine to obtain
$N^2$-(4-tert-butyl-benzyl)-7-chloro-$N^4$-(4-diethylamino-1-methyl-butyl)-quinazoline-2,4-diamine.

Analogously to example 17, 2,4,7-trichloro-quinazoline is reacted with 2-pyridin-2-yl-ethylamine to give (7-chloro-quinazolin-4-yl)-(2-pyridin-2-yl-ethyl)-amine and is further reacted
with phenethylamine to obtain
7-chloro-$N^2$-phenethyl-$N^4$-(2-pyridin-2-yl-ethyl)-quinazoline-2,4-diamine;
with 3-morpholin-4-yl-propylamine to obtain
7-chloro-$N^2$-(3-morpholin-4-yl-propyl)-$N^4$-(2-pyridin-2-yl-ethyl)-quinazoline-2,4-diamine.

Analogously to example 17, 2,4,7-trichloro-quinazoline is reacted with diethylamine to give (2,7-dichloro-quinazolin-4-yl)-diethyl-amine and is further reacted
with biphenyl-4-ylamine to obtain
$N^2$-biphenyl-4-yl-7-chloro-$N^4,N^4$-diethyl-quinazoline-2,4-diamine.

The following examples relate to pharmaceutical preparations:

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is melted with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The mixture is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 g of talc and 0.1 kg of magnesium stearate is compressed in a customary manner to give tablets such that each tablet contains 10 mg of active compound.

Example F

Coated Tablets

Analogously to Example E, tablets are pressed which are then coated with a coating of sucrose, potato starch, talc, tragacanth and colorant in a customary manner.

Example G

Capsules 2 kg of active compound of the formula I are dispensed into hard gelatin capsules in a customary manner such that each capsule contains 20 mg of the active compound.

Example H

Ampules

A solution of 1 kg of active compound of the formula I in 60 ml of double-distilled water is sterile-filtered, dispensed into ampoules, lyophilized under sterile conditions and aseptically sealed. Each ampule contains 10 mg of active compound.

What is claimed is:
1. Compounds of the formula I

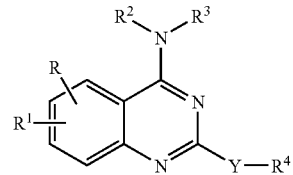

in which
R and $R^1$ are independently of each other H, alkyl of 1-6 carbon atoms, $OR^5$, Hal, $N(R^5)_2$, $NO_2$, CN, CHO, COalkyl of 1-6 carbon atoms, $CON(R^5)_2$, $COOR^5$, allyl, CH=CH—$COOR^5$, CH=CHCON$(R^5)_2$, $SO_2$alkyl of 1-6 carbon atoms or phenyl, which is unsubstituted or mono-, di- or trisubstituted by alkyl of 1-6 carbon atoms,
$R^2$ is H, alkyl of 1-6 carbon atoms, cycloalkyl, —$(CH_2)_o$—$OR^5$, or —$(CH_2)_o$—$OR^6$,
$R^3$ is

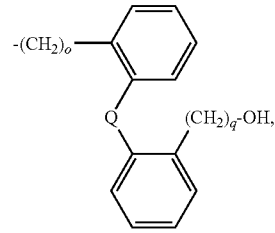

$R^4$ is Ar,
$R^5$ is H or alkyl of 1-6 carbon atoms,
$R^6$ is benzo[1,3]dioxol-5-yl,
$R^7$ is H, alkyl of 1-6 carbon atoms, cycloalkyl or $(CH_2)_q$—$OR^5$,
Q is S,
Y is a direct bond,
Ar is phenyl, naphthyl or biphenyl, which is unsubstituxed or mono-, di- or trisubstituted by alkyl of 1-6 carbon atoms, $OR^5$, cycloalkyloxy, O—$(CH_2)_p$-Ph, $CF_3$, $OCF_3$, Hal, CN, CHO, COalkyl of 1-6 carbon atoms, $COOR^5$, —$(CH_2)_p$—$N(R^7)_2$, $NR^5$—COalkyl of 1-6 carbon atoms, $NO_2$, $SO_2N(R^5)_2$, mor, $SO_2$-mor, 5-methyl-3-oxo-2,4-dihydropyrazol-2-yl, naphthyl or $Her^2$,
$Het^2$ is a unsaturated mono- or bicyclic heterocyclic radical having 5 to 10 ring members, where 1 or 2 N and/or 1 or 2 S or O atoms can be present and the heterocyclic radical can be mono- or disubstituted by alkyl of 1-6 carbon atoms, Hal, $OR^5$, $CF_3$, $OCF_3$, $N(R^5)_2$, —$(CH_2)_p$—(CHalkyl of 1-6 carbon atoms)$_q$-$N(R^5)$—$(CH_2)_q$—$COR^5$, CHO, COalkyl of 1-6 carbon atoms or $COOR^5$,
Hal is F, Cl, Br or I,
mor is morpholin-4-yl, Ph is phenyl,
o is 1, 2, 3, 4, 5, 6 or 7,
p is 0, 1, 2, 3 or 4,
q is 1, 2, 3 or 4,
and their pharmaceutically acceptable salts.

2. The compound according to claim 1 wherein R is H, or alkoxy.

3. The compound according to claim 1 wherein $R^1$ is H, alkyl, alkoxy or halo.

4. A pharmaceutical composition comprising a pharmaceutically acceptable carrier and as an active ingredient a therapeutically effective amount of a compound as claimed in claim 1.

* * * * *